US011219901B2

(12) United States Patent
Picart et al.

(10) Patent No.: US 11,219,901 B2
(45) Date of Patent: Jan. 11, 2022

(54) ROBOTIC METHOD FOR COATING A MULTIWELL PLATE BY A POLYELECTROLYTE MULTILAYER FILM

(71) Applicants: INSTITUT POLYTECHNIQUE DE GRENOBLE, Grenoble (FR); Centre national de la recherche scientifique, Paris (FR)

(72) Inventors: Catherine Cécile Picart, Grenoble (FR); Jie Liu, Saint Martin le Vinoux (FR); Fabien Dalonneau, Laval (FR); Paul Machillot, Fontaine (FR)

(73) Assignees: INSTITUT POLYTECHNIQUE DE GRENOBLE, Grenoble (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 35 days.

(21) Appl. No.: 16/468,806

(22) PCT Filed: Dec. 15, 2017

(86) PCT No.: PCT/EP2017/083092
§ 371 (c)(1),
(2) Date: Jun. 12, 2019

(87) PCT Pub. No.: WO2018/109184
PCT Pub. Date: Jun. 21, 2018

(65) Prior Publication Data
US 2020/0094246 A1 Mar. 26, 2020

(30) Foreign Application Priority Data
Dec. 15, 2016 (EP) .................................. 16306697

(51) Int. Cl.
*B01L 3/00* (2006.01)
*C12M 1/32* (2006.01)
*C12M 1/00* (2006.01)

(52) U.S. Cl.
CPC ........... *B01L 3/5085* (2013.01); *C12M 23/12* (2013.01); *C12M 23/20* (2013.01);
(Continued)

(58) Field of Classification Search
CPC .......... A61L 27/00; B01L 3/5085; B01L 3/00
See application file for complete search history.

(56) References Cited

U.S. PATENT DOCUMENTS

| 6,340,595 B1 * | 1/2002 | Vogels ............... C12N 15/1034 435/235.1 |
| 2005/0191430 A1 * | 9/2005 | Rubner .................. A61L 27/34 427/407.1 |
| 2005/0226782 A1 * | 10/2005 | Reed .................. B01L 3/50851 422/400 |

FOREIGN PATENT DOCUMENTS

| EP | 1535952 A1 | 6/2005 |
| WO | 2010081884 A2 | 7/2010 |

OTHER PUBLICATIONS

Search Report for European Application No. EP 16 30 6697 dated Nov. 20, 2017.
(Continued)

Primary Examiner — Dah-Wei D. Yuan
Assistant Examiner — Andrew J Bowman
(74) Attorney, Agent, or Firm — Pearne & Gordon LLP

(57) ABSTRACT

The invention concerns a robotic method for coating the bottom surface of at least one well of a multiwell plate by a polyelectrolyte multilayer film, the multiwell plate obtainable according to the method and the use thereof for cell culture.

15 Claims, 14 Drawing Sheets

Figure 1:
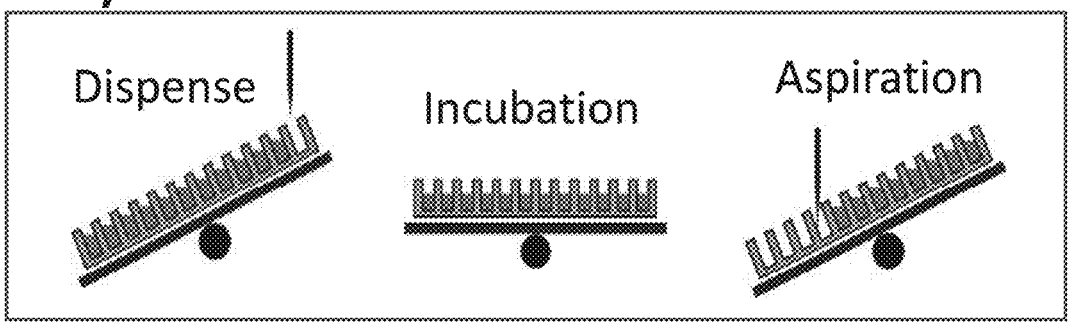
Figure 1:
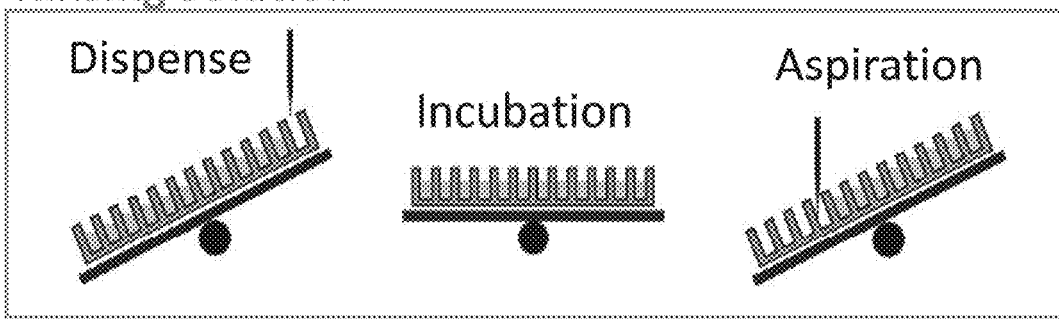
Figure 1:
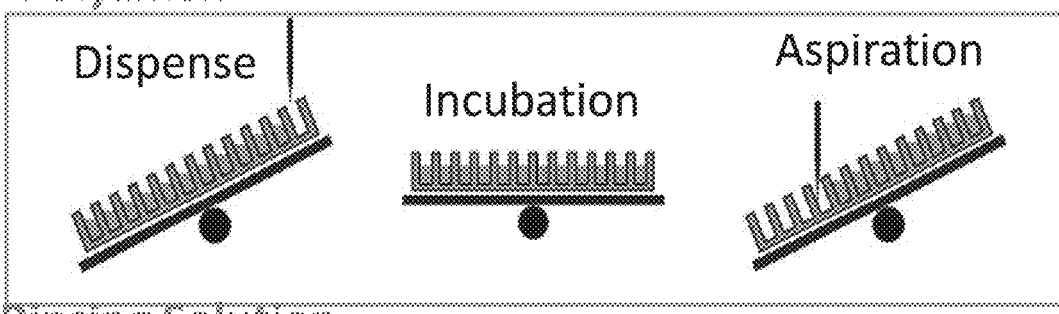
Figure 1:
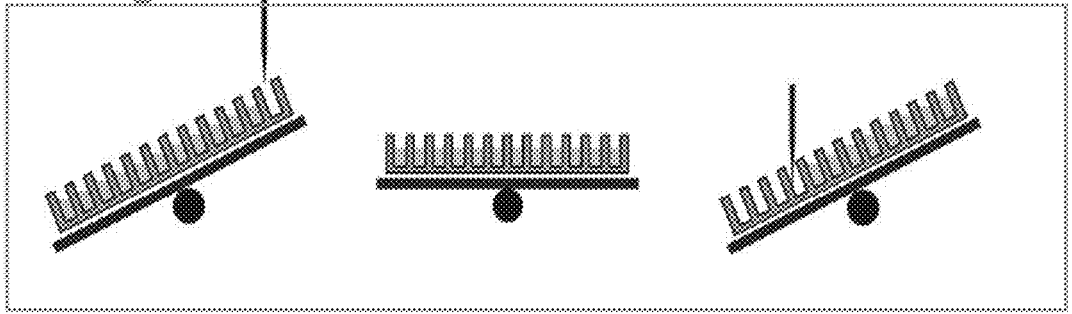

(52) U.S. Cl.
CPC ... *B01L 2200/0642* (2013.01); *B01L 2200/12* (2013.01); *B01L 2300/16* (2013.01); *C12N 2533/30* (2013.01)

(56) References Cited

OTHER PUBLICATIONS

Search Report for International No. PCT/EP2017/083092 dated Mar. 20, 2018.

Jaklenex, Ana et al., "High Throughput Layer-by-Layer Films for Extracting Film Forming Parameters and Modulating Film Interactions with Cells", ACS Appl. Mater. Interfaces, 2016, pp. 2255-2261, vol. 8, DOI: 10.1021/acsami.5b11081.

Thomas Crouzier et al., "Layer-By-Layer Films as a Biomimetic Reservoir for rhBMP-2 Delivery: Controlled Differentiation of Myoblasts to Osteoblast**", 2009, X No. X, pp. 1-11, Wiley-VCH Verlag GmbH & Co. KGaA, Weinheim, www.small-journal.com.

* cited by examiner

Polycation

Rinsing Solution

Polyanion

Rinsing Solution

Fig 26
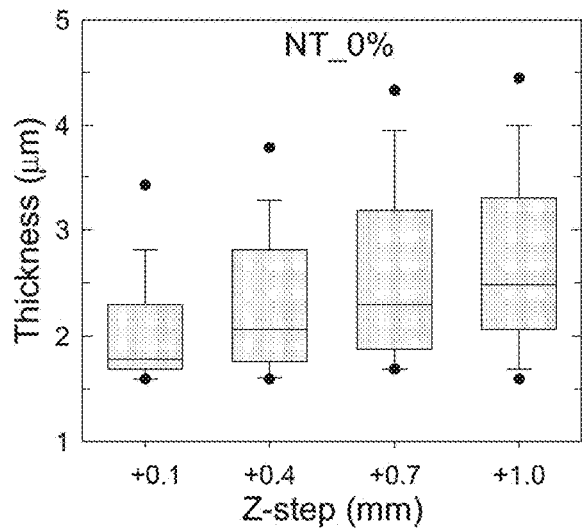
Fig 27
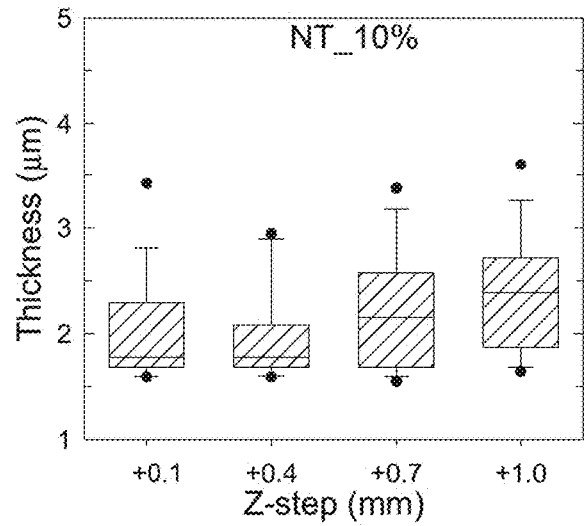
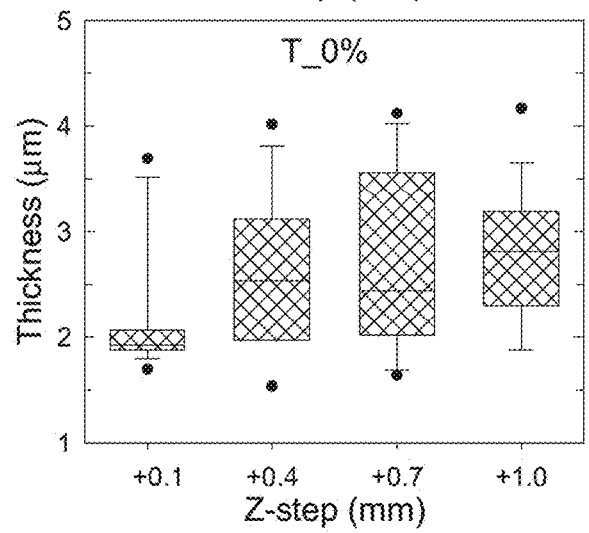
Fig 28
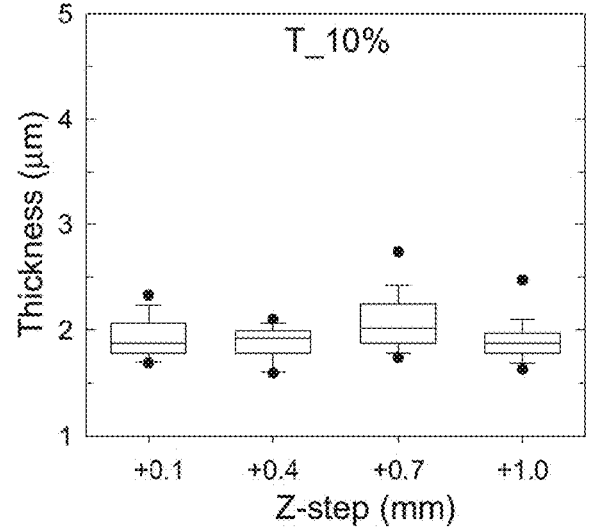
Fig 29

ROBOTIC METHOD FOR COATING A MULTIWELL PLATE BY A POLYELECTROLYTE MULTILAYER FILM

CROSS-REFERENCE TO RELATED APPLICATIONS

This is a National Stage application of PCT international application PCT/EP2017/083092, filed on Dec. 15, 2017, which claims the priority of European Patent Application No. 16306697.0, filed Dec. 15, 2016, both of which are incorporated herein by reference in their entirety.

The present invention concerns a robotic method for coating a multiwell plate by a polyelectrolyte multilayer film allowing the preparation of films in a highly reproducible and reliable manner and with a very high spatial homogeneity.

The deposition of polyelectrolyte multilayer (PEM) has emerged as a very easy handling and versatile tool. Based on the alternate adsorption of polycations and polyanions, this technique allows to buildup films with tunable properties: by adjusting several parameters such as the chemical nature of the polyelectrolytes, pH and ionic strength, immersion and rinsing times, post-treatment of the film, it is possible to obtain an almost infinite variety of architectures.

The electrostatic layer-by-layer (LbL) assembly technique has recently emerged as a very promising tool for biomedical applications in view of its versatility, notably the large range of building blocks and assembly conditions, and the possibility to deliver locally small therapeutics and proteins, such as growth factors. The large range of templates (shape, size), of layer materials (biologic or synthetic) available for surface modification and the impressive panel of LbL assembly technologies have all contributed to the widespread use of the technique.

Application EP 1535952 discloses a method for preparing cross-linked polyelectrolyte multilayer films, comprising the reaction of complementary functional groups: carboxylic groups and amino groups, present in the polymers that constitute the multilayer film, in the presence of a coupling agent, whereby amide bonds are formed.

Application WO 2010/081884 discloses a method for coating a surface, comprising the following steps: (a) sequentially depositing on a surface at least one layer of alternate adsorbed polyelectrolytes to provide a coated surface presenting complementary amino and carboxylic reactive groups, wherein a first (or conversely second) polyelectrolyte is a cationic polymer comprising said amino groups and a second (or conversely first) polyelectrolyte is an anionic polymer comprising said carboxylic groups, (b) reacting said complementary reactive groups of the coated surface in the presence of a coupling agent, as to form amide bonds between said complementary reactive groups giving rise to a cross-linked polyelectrolyte multilayer film, and (c) treating said cross-linked polyelectrolyte multilayer film with a protein containing solution, preferably with a growth factor type protein containing solution, as to incorporate said protein on and inside said cross-linked polyelectrolyte multilayer film. The obtained film thus contains proteins. Films were constructed in 96 well plates, but manually using a multiple channel pipette for dispense and aspiration steps. However, this process is user-dependent and thus not reproducible, time-consuming and susceptible to human errors.

A variety of strategies have already been developed to automate LbL films deposition. While the most popular techniques are dip coating, spraying and spin coating, these technologies are rather suited for large substrates, require a significant volume of liquid and cannot be adapted to cell culture plates.

Recently, Jaklenec et al. (ACS Appl Mater Interfaces, 2016, 8(3):2255-61) used an automated liquid handling robot, to prepare polyelectrolyte films from synthetic polymers (polyacrylic acid/polyallylamine hydrochloride, PAA/PAH) over a large pH range and containing increasing number of layers. To this end, the polyelectrolyte films were built on (bottomless) silicon 96 well plates glued to silicon wafer, in order to be subsequently analyzed by profilometry and used to screen for cell attachment and spreading. However, the authors identified several remaining technical problems: i) radial heterogeneity in film thickness, in particular coffee ring effect; ii) difficulty to automate characterization and analysis of the film. Also, there was neither characterization of the polyelectrolyte films in situ in the cell culture plates, nor proofs that bioactive molecules can be loaded in films and be effectively bioactive.

Accordingly, the development of an automated electrostatic layer-by-layer assembly technique in multiple-well plates allowing the preparation of films:
  in a highly reproducible and reliable manner,
  with a very high spatial homogeneity inside each well and between different wells in order to optimize cell culture,
is still required.

For this purpose, the present invention concerns a method for coating the bottom surface of at least one well of a multiwell plate by a polyelectrolyte multilayer film, said method comprising n successive sequences, n being an integer from 1 to 2000, wherein each sequence comprises the steps of:
a) robotic deposit of a volume $V_{PE}^1$ of a solution of a first polyelectrolyte $PE^1$ on the bottom surface of at least one well of a multiwell plate, wherein the first polyelectrolyte $PE^1$ is either a cationic polymer comprising amino groups, or an anionic polymer, then
b) robotic aspiration of an aspirated volume $V_{aspPE}^1$ of said solution of $PE^1$, wherein the aspirated volume $V_{aspPE}^1$ is higher than or equal to $V_{PE}^1$, then
c) robotic deposit of a volume $V_{PE}^2$ of a solution of a second polyelectrolyte $PE^2$ on said bottom surface, wherein the second polyelectrolyte $PE^2$ is a cationic polymer comprising amino groups when $PE^1$ is an anionic polymer, or $PE^2$ is an anionic polymer when $PE^1$ is a cationic polymer comprising amino groups, then
d) robotic aspiration of an aspirated volume $V_{aspPE}^2$ of said solution of $PE^2$, wherein the aspirated volume $V_{aspPE}^2$ is higher than or equal to $V_{PE}^2$.

The robotic steps are typically carried out with an automated liquid handling machine provided with pipetting arm as robot, for example with a TECAN Freedom EVO® 100 robot. The ends of the arms of the robots are provided with tips which allow depositing and aspirating solutions. The liquid handling arm pipettes the solutions in their respective reservoirs and dispensed them in selected wells. After being aspirated, the solutions are thrown in a trash.

Steps a) and c) are dispense steps. At step a), the robot aspirates the solution of the first polyelectrolyte $PE^1$ from a reservoir containing said solution and transfers said solution to the bottom surface of at least one well of the multiwell plate. At step c), the robot aspirates the solution of the second polyelectrolyte $PE^2$ from a reservoir containing said solution and transfers said solution to the bottom surface of the well(s) of the multiwell plate. Preferably, to implement steps a) and c), the ends of the arms of the robots are provided with 1 mL pipette tips.

Steps b) and d) are aspiration steps. At step b) and d), the robot aspirates the solution from the well and transfers it to the trash. Preferably, to implement steps b) and d), the ends of the arms of the robots are provided with 200 μL pipette tips. These smaller tips allow a better accuracy of the aspiration steps and thus a better homogeneity of the obtained film.

The typical pipetting speed is from 400 to 800 μL/s for dispense steps a) and c) and from 30 to 150 μL/s for aspiration steps b) and d).

Preferably, each sequence of the method comprises:
between steps a) and b), a step a') of incubation wherein the solution of first polyelectrolyte $PE^1$ is left in contact with the bottom surface for a duration from 1 to 30 minutes, preferably from 5 to 15 minutes, and
between steps c) and d), a step c') of incubation wherein the solution of second polyelectrolyte $PE^2$ is left in contact with the bottom surface for a duration from 1 to 30 minutes, preferably from 5 to 15 minutes.

The method comprises steps b) and d) of robotic aspiration of an aspirated volume $V_{aspPE}$ of the solution of PE, wherein the aspirated volume $V_{aspPE}$ is higher than or equal to $V_{PE}$, PE being either $PE^1$ step b) or $PE^2$ (step d)).

In one embodiment, $V_{aspPE}^1 = V_{PE}^1$ and $V_{aspPE}^2 = V_{PE}^2$.

In another embodiment, $V_{aspPE}^1$ is higher than $V_{PE}^1$ and $V_{aspPE}^2$ is higher than $V_{PE}^2$. Typically, $V_{aspPE}^1$ and $V_{aspPE}^2$ are respectively higher than $1.01 \times V_{aspPE}^1$ and $1.01 \times V_{aspPE}^2$, notably higher than $1.02 \times V_{aspPE}^1$ and $1.02 \times V_{aspPE}^2$, for example higher than $1.05 \times V_{aspPE}^1$ and $1.05 \times V_{aspPE}^2$, most preferably around $1.10 \times V_{aspPE}^2$. Generally, $V_{aspPE}^1$ and $V_{aspPE}^2$ are respectively lower than $1.50 \times V_{aspPE}^1$ and $1.50 \times V_{aspPE}^2$.

This means that the arm of the robot aspirates an additional aspiration volume compared to the volume of solution which has been deposited. In fact, the robot aspirates a mixture of solution which has been deposited and of air.

The present invention is based on the discovery that aspirating a volume higher than or equal to the volume of solution which was deposited leads to a film having a high spatial homogeneity, i.e. not only a high spatial homogeneity of the film deposited inside each individual well, but also to a high reproducibility of the film deposit between different wells (within a single plate and in different plates built in independent runs of the automated machine).

Using a robotic arm equipped with multiple channels enables to automate the layer-by-layer deposit method and to optimize the workflow. Parallel processing provides several key advantages for the LbL film buildup: i) ensuring the reproducibility of the deposit, ii) enhancing the throughput for cell screening assays, iii) being adaptable to any type of robotic arm whatever the manufacturer.

The implementation of the method according to the invention on commercially available liquid handling machines will undoubtedly broaden the range of possibilities offered by the well-controlled LbL coatings in view of applications in biomolecular or cellular screening for biotechnologies and regenerative medicine.

The method involves a multiwell plate, for example 6-, 12-, 24-, 48- or 96-well plates. The 96-well plate format is particularly interesting in view of cell screening assays, since multiple conditions can be screened in parallel and the number of cells needed per well is small (typically 5000 cells/well or less).

It is possible to implement the method on all wells of the multiwell plate, or only on some of them (preferably at least on two wells).

The wells chosen for the deposit at step a) of the first sequence are the wells of the multiwell plate on which the multilayer film is formed. Generally, all the steps of the method are carried out on the same wells, m being the number of wells selected by the used to implement the method. Accordingly, m is an integer from 1 (embodiment wherein the method is implemented in only one well) to the number of wells of the multiwell plate (for example 96 for a 96-well plate), preferably from 2 to the number of wells of the multiwell plate. Indeed, in order to build the layer pairs of the multilayer film, the deposit or aspirations of steps b), c) and d) are carried out on the same wells than the wells on the bottom surface of which the solution of the first polyelectrolyte $PE^1$ is deposited at step a) of the first sequence. Similarly, all the steps of all the sequences involve the same wells than the one chosen at step a) of the first sequence. The software of the automated handling robot allows defining the number of wells m and specific positions where the layer-by-layer film must to be deposited.

All the wells of the plate have a height H. The bottom of the wells may have various forms, U form, V form or planar round from. The wells preferably have a planar bottom, usually a round bottom surface having a diameter d.

Each sequence of the method allows depositing a layer pair of the multilayer film. The multilayer film obtained at the end of the method comprises n layer pairs.

The number "n" of layer pairs in polyelectrolyte multilayer film prepared through the method can vary in a wide range and depend on the desired thickness. Preferably, n is an integer from 2 to 2000, in particular from 5 to 2000, preferably from 5 to 1000, more preferably from 5 to 100. When a thick polyelectrolyte film is desired, n can vary from 15 to 1000, preferably from 20 to 500 (in particular from 20 to 60).

Each layer pair comprises a layer of polyelectrolyte $PE^1$ and a layer of polyelectrolyte $PE^2$ of opposite charge. The film architecture is precisely designed and can be controlled to 1 nm precision with a range from 1 to 50000 nm, preferably from 100 nm to 30 μm. The thickness of the film can generally vary from 1 nm to 50000 nm, preferably from 500 nm to 20 μm, more preferably from 1 to 10 μm. A film is considered as a thick film when its thickness is more than 300 nm.

The method comprise depositing sequentially a first polyelectrolyte $PE^1$, then a second polyelectrolyte $PE^2$, one of them being a cationic polymer comprising amino groups, and the other being an anionic polymer.

In the present invention, the terms "anionic polymer" relate to a polymer comprising at least one group susceptible to bear a negative charge. The anionic polymer preferably comprises carboxylic, phosphate, sulfate and/or sulfonate groups. The carboxylic groups can be present in the form of acids, acid halide (preferably, acid chloride), acid anhydride or activated esters, such as N-hydroxysulfosuccinimide ester or n-paranitrophenyl ester. The anionic groups are covalently bond to the used polymers.

Any anionic polymer can be used in the method, including, without limitation thereto, poly(acrylic) acid, poly (methacrylic) acid, poly(glutamic) acid, polyuronic acid (alginic, galacturonic, glucuronic, . . . ), glycosaminoglycans (hyaluronic acid or a salt thereof (such as sodium)—also called hyaluronan-, dermatan sulphate, chondroitin sulphate, heparin, heparan sulphate, keratan sulphate), poly(aspartic acid) and Polystyrene sulfonate (PSS), any combination of the polyamino-acids (in the D and/or L forms), and mixtures thereof.

The terms "cationic polymer" relate to a polymer comprising at least one group susceptible to bear a positive charge.

In the sense of the invention, the amino groups can be present in the form of hydroxylamine, hydrazide and amine functions. The amino groups are covalently bond to the used polymers.

Any cationic polymer comprising amino groups can be used in the method, including, without limitation thereto, poly(lysine), such as poly(D-, L-lysine), poly(diallydimethylammonium chloride), poly(allylamine), poly(ethylene) imine, chitosan, polyarginine, such as Poly(L-arginine), Poly(ornithine), polyhistidine, such as Poly(D,L-histidine), poly(mannosamine), polyallylamine hydrochloride (PAH) and more generally any combination of the polyamino acids (in the D and/or L forms), and mixtures thereof.

Preferably, the cationic polymer comprising amino group is poly(L-lysine) (or PLL), polyallylamine hydrochloride (PAH) or chitosan (CHI) and/or the anionic polymer comprising amino group is the hyaluronic acid or a salt hereof, such as hyaluronan sodium (also called generally HA), heparin (HEP), polystyrene sulfonate (PSS), poly(L-glutamic acid) (PGA) or a mixture thereof.

The polyelectrolyte multilayer film is more preferably a (PLL/HA) film, a (PSS/PAH) film, a (PLL/PGA) or a (CHI/PGA) film.

The molecular weight of the polymers identified above can vary in a wide range. More preferably, the molecular weight is in the range from 0.5 kDa to 20,000 kDa, even more preferably, the molecular weight is in the range from 5 to 2,000 kDa.

Generally, the same polyelectrolytes $PE^1$ and $PE^2$ are used for all the sequences.

Generally, the same solution of first polyelectrolyte $PE^1$ is used for all steps a) of each sequence, and the same solution of second polyelectrolyte $PE^2$ is used for all steps c) of each sequence.

Generally, $V_{PE}^1$ is the same for all the sequences, $V_{aspPE}^1$ is the same for all the sequences, $V_{PE}^2$ is the same for all the sequences and $V_{aspPE}^2$ is the same for all the sequences.

Generally, the method comprises at least a rinsing step after each polyelectrolyte deposit step. Accordingly, the method usually comprises:
between steps b) and c) of each sequence, a rinsing step comprising the following substeps:
b2) robotic deposit of a volume $V_{rinsePE}^1$ of a rinsing solution on said bottom surface, then
b3) robotic aspiration of an aspirated volume $V_{asprinsePE}^1$ of said rinsing solution, wherein the aspirated volume $V_{asprinsePE}^1$ is higher than or equal to $V_{rinsePE}^1$,
wherein the rinsing step can be repeated, and
after step d) of each sequence, a rinsing step comprising the following substeps:
d2) robotic deposit of a volume $V_{rinsePE}^2$ of a rinsing solution on said bottom surface, then
d3) robotic aspiration of an aspirated volume $V_{asprinsePE}^2$ of said rinsing solution, wherein the aspirated volume $V_{asprinsePE}^2$ is higher than or equal to $V_{rinsePE}^2$,
wherein the rinsing step can be repeated.

At steps b2) and d2, the robot aspirates the rinsing solution from a reservoir containing said solution and transfers said solution to the bottom surface of the well(s) of the multiwell plate. Preferably, to implement steps b2) and d2), the ends of the arms of the robots are provided with 1 mL pipette tips.

At steps b3) and d3), the robot aspirates the solution from the well and transfers it to the trash. Preferably, to implement steps b3) and d3), the ends of the arms of the robots are provided with 200 µL pipette tips.

Usually, when $V_{aspPE}^1 = V_{PE}^1$ and $V_{aspPE}^2 = V_{PE}^2$, then $V_{asprinsePE}^1 = V_{rinsePE}^1$ and $V_{asprinsePE}^2 = V_{rinsePE}^2$. In the same way, usually, when $V_{aspPE}^1$ is higher than $V_{PE}^1$ and $V_{aspPE}^2$ is higher than $V_{PE}^2$, then $V_{asprinsePE}^1$ is higher than $V_{rinsePE}^1$ and $V_{asprinsePE}^2$ is higher than $V_{rinsePE}^2$. Typically, the same additional volume percentage is used for all of them. In other words, typically, $V_{aspPE}^1 = \beta \times V_{PE}^1$, $V_{aspPE}^2 = \beta \times V_{PE}^2$, $V_{asprinsePE}^1 = \beta \times V_{rinsePE}^1$ and $V_{asprinsePE}^2 = \beta \times V_{rinsePE}^2$, wherein $\beta$ is a number from 1.00 (i.e. no additional volume aspirated) to 1.30.

Preferably, when the method comprises these rinsing steps, each sequence thereof also comprises:
between steps b2) and b3), a step b2') of incubation wherein the rinsing solution is left in contact with the bottom surface for a duration from 0.2 to 10 minutes, preferably from 1 to 5 minutes, and
between steps d2) and d3), a step d2') of incubation wherein the rinsing solution is left in contact with the bottom surface for a duration from 0.2 to 10 minutes, preferably from 1 to 5 minutes.

Generally, the same rinsing solution is used for all steps b2') for all the sequences and the same rinsing solution is used for all steps d2') for all the sequences.

If possible, the rinsing solution used at step b2) is the same than the one used at step d2), since this facilitates the method. Generally, when the same rinsing solution is used both for steps b2) and d2), the method involves three solutions: the solution of a first polyelectrolyte $PE^1$, the solution of second polyelectrolyte $PE^2$ and the rinsing solution used both for steps b2) and d2).

If different rinsing solutions are required at steps b2 and d2), the method typically involves four solutions: the solution of a first polyelectrolyte $PE^1$, the solution of second polyelectrolyte $PE^2$, and the rinsing solution used for step b2) and the rinsing solution used for step d2).

Suitable solvents for polyelectrolyte solutions and rinsing solutions are: water, aqueous solutions of salts (for example NaCl, KCl, $MnCl_2$, $(NH_4)_2SO_4$), any type of physiological buffer (Hepes, phosphate buffer, culture medium such as minimum essential medium, Mes-Tris, Mes, Tris, buffers) and water-miscible, non-ionic solvents, such as C1-C4-alkanols, C3-C6-ketones including cyclohexanone, tetrahydrofuran, dioxane, dimethyl sulphoxide, ethylene glycol, propylene glycol and oligomers of ethylene glycol and propylene glycol and ethers thereof and open-chain and cyclic amides, such as dimethylformamide, dimethylacetamide, N-methylpyrrolidone and others. Polar, water-immiscible solvents, such as chloroform or methylene chloride, which can contain a portion of the abovementioned organic solvents, insofar as they are miscible with them, will only be considered in special cases. Water or solvent mixtures, one component of which is water, are preferably used. If permitted by the solubility of the polyelectrolytes implemented, only water is used as the solvent, since this simplifies the method.

In order to improve further spatial homogeneity of the film formed, two different embodiments have been developed and are described hereafter:

In a first embodiment, called "wet surface" hereafter, a volume $V_{wet}$ of the first polyelectrolyte $PE^1$ solution is added initially (i.e. prior to buildup of the film, prior to the sequences described above) to each well, typically in order to form a liquid layer recovering the bottom surface.

In this first embodiment, in the method defined above, prior to step a) of the first sequence, the at least one well on which step a) will be carried out is filled with a volume $V_{wet}$ of the solution of the first polyelectrolyte $PE^1$, wherein the volume $V_{wet}$, expressed in mL, is from:

$$V_{wet}^{min}=0.5\times\pi(d/2)^2$$

to $$V_{wet}^{max}=(2/3)\times\pi(d/2)^2\times H,$$

wherein:
d is the diameter of the well, expressed in mm,
H is the height of the well, expressed in mm.

The volume $V_{wet}$ depends on the diameter (d) and height (H) of the wells of the multiwell plate.

The volume $V_{wet}$ is higher than or equal to $V_{wet}^{min}=0.5\times\pi(d/2)^2$, which corresponds to a volume allowing a liquid height of 0.5 mm, which is considered to be the lowest liquid height.

The volume $V_{wet}$ is lower than or equal to $V_{wet}^{max}=(2/3)\times\pi(d/2)^2\times H$, which corresponds to a volume allowing a liquid height of (2/3) of the height of the well. Preferably, the volume $V_{wet}$ is lower than or equal to $(1/2)\times\pi(d/2)^2\times H$, or even lower than or equal to $(1/3)\times\pi(d/2)^2\times H$.

Table 1 below provides examples of usual heights and diameters of multiwell plates and the corresponding $V_{wet}^{min}$ and $V_{wet}^{max}$.

TABLE 1 usual H and d of multiwell plates and corresponding $V_{wet}^{min}$ and $V_{wet}^{max}$

| Number of wells | 96 wells | 48 wells | 24 wells | 12 wells | 6 wells |
|---|---|---|---|---|---|
| Height H (mm) | 11.20 | 16.84 | 17.80 | 18.00 | 17.67 |
| diameter d (mm) | 6.40 | 11.00 | 15.60 | 22.10 | 34.80 |
| Total volume/well (µL) | 360.00 | 1600.00 | 3400.00 | 6900.00 | 16800.00 |
| $V_{wet}^{min}$ (µL) | 16.1 | 47.5 | 95.5 | 191.7 | 475.4 |
| $V_{wet}^{max}$ (µL) | 240.0 | 1066.7 | 2266.7 | 4600.0 | 11200.0 |

Preferably, the volume $V_{wet}$ is the minimal recommended working volume of the multiwell plate, i.e. the minimal working volume recommended on the data sheet of the multiwell plate.

Two alternatives are possible to obtain a well filled with a volume $V_{wet}$ of a solution of the first polyelectrolyte $PE^1$.

According to one alternative, the method comprises, prior to step a) of the first sequence, a step a0) of robotic deposit of a volume $V_{wet}$ of the solution of the first polyelectrolyte $PE^1$ on the bottom surface of each well on which the deposit will be carried out at step a) of the first sequence.

This alternative is interesting in that only one additional step is necessary.

According to a second alternative, the method comprises, prior to step a) of the first sequence, the steps of:
a1) robotic deposit of a volume $V_{a1)}$ of the solution of the first polyelectrolyte $PE^1$ on the bottom surface of each well on which the deposit will be carried out at step a) of the first sequence, wherein $V_{a1)}$ is higher than $V_{wet}$, then
a2) robotic aspiration of an aspirated volume $V_{a2)}$ of said solution of the first polyelectrolyte $PE^1$, wherein the aspirated volume $V_{a2)}$ is as such that:

$$V_{a2)}=V_{a1)}-V_{wet}.$$

This second alternative thus requires two additional steps before carrying out the n sequences. It is however interesting because it allows a homogeneous distribution of the solution on the bottom surface. Accordingly, this alternative is interesting when the volume $V_{wet}$ is close to $V_{wet}^{min}$, because low volumes of solution are more difficult to distribute all over the surface of the bottom surface.

Usually, to ensure that the aspirated volume $V_{a2)}$ is equal to $V_{a1)}$ minus $V_{wet}$, the end of the tip of the robot which is used to aspirate the solution is immersed into the solution. Accordingly, no air is aspirated and the aspirated volume, which is entered into the robot, is $V_{a2)}$.

In this first embodiment, particularly preferred is $V_{aspPE}^1=V_{PE}^1$ and $V_{aspPE}^2=V_{PE}^2$. In this case, a constant volume of solution (i.e. $V_{wet}$) is left inside each well, which ensures that the surface always remains covered by liquid. By doing so, local differences in the wet/dry state above the polyelectrolyte film are avoided, and more homogeneous films are obtained. Moreover, since there is a permanent liquid film inside each well wherein the film is formed, no optimization of the distance between the end of the tip of the robots' arm and the bottom surface is required.

Typically, in this first embodiment of the method, each rinsing step is repeated three times (i.e. each sequence of the method comprises, in that order, steps a), b), b2), b3), b2), b3), b2), b3), b2), b3), c), d), d2), d3), d2), d3), d2), d3), d2) and d3)). As a constant volume of solution (i.e. $V^{wet}$) is left inside each well, numerous rinsing steps are required for an effective rinsing.

In a second embodiment, called "tilting" hereafter, the plate is tilted (FIG. 1) in order to improve liquid homogeneity during the deposit and aspiration steps.

In this second embodiment, for each sequence of the method according to this second embodiment, at steps a), b), c), d), and, if these steps are present, at steps b2), b3), d2) and d3), the bottom surface is tilted with an inclination angle α from 5 to 40° preferably from 10 to 30°, more preferably around 20°, relative to the horizontal plane. Preferably, the angle α is the same for all the steps a), b), c), d), and, if these steps are present, for steps b2), b3), d2) and d3). This tilting helps removing all the liquid from the well during the aspiration steps.

Typically, to tilt the bottom surface, the plate carrier is tilted with the inclination angle α (FIG. 1).

Preferably, during the incubation steps defined above, the bottom surface is within the horizontal plane (i.e. the bottom surface is not tilted). Accordingly, preferably, for each sequence, when each sequence comprises steps a') and c') as defined above and/or comprises steps b2') and d2') as defined above, then, for each sequence, at steps a') and c'), and/or at steps b2') and d2'), the bottom surface is within the horizontal plane. This also helps obtaining a homogeneous film, because the liquid is spread homogeneously at the bottom surface of the well.

Typically, the multiwell plate is tilted to implement step a), then moved back to an horizontal plane to implement step a'), then tilted to implement steps b) and b2), then moved back to an horizontal plane to implement step b2'), then tilted to implement steps b3) and c), then moved back to an horizontal plane to implement step c'), then tilted to implement steps d) and d2), then moved back to an horizontal plane to implement step d2'), then tilted to implement step d3) (FIG. 1).

Typically, in this second embodiment of the method, each rinsing step is repeated once (i.e. each sequence of the method comprises, in that order, steps a), b), b2), b3), b2), b3), c), d), d2), d3), d2) and d3)). Typically, the multiwell plate is tilted to implement step a), then moved back to an horizontal plane to implement step a'), then tilted to implement steps b) and b2), then moved back to an horizontal plane to implement step b2'), then tilted to implement steps b3) and b2), then moved back to an horizontal plane to implement step b2'), then tilted to implement steps b3) and c), then moved back to an horizontal plane to implement step c'), then tilted to implement steps d) and d2), then moved back to an horizontal plane to implement step d2'), then tilted to implement step d3) and d2), then moved back to an horizontal plane to implement step d2'), then tilted to implement step d3).

In this second embodiment of the method, $V_{aspPE}^1$ can be equal to $V_{PE}^1$ and $V_{aspPE}^2$ can be equal to $V_{PE}^2$. However, in that case, a better homogeneity is obtained when the distance between the end of the tip of the robots' arm and the bottom surface is lower than 0.3 mm. Moreover, the inventors discovered that it is very difficult to remove all the volume of solution of polyelectrolyte which was initially deposited, and that the remaining solution causes heterogeneity.

In order to avoid this difficulty and to improve further the homogeneity of the film, optimizing the aspiration of the volume in each well by tilting is preferably combined with aspiration of an additional volume, which enables to efficiently suck all the liquid from the well by aspirating virtually an excess volume. Accordingly, the aspirated volume $V_{aspPE}^1$ is preferably higher than $V_{PE}^1$, notably from $1.05\ V_{PE}^1$ to $1.20 \times V_{PE}^1$ and the aspirated volume $V_{aspPE}^2$ is preferably higher than $V_{PE}^2$, notably from $1.05\ V_{PE}^2$ to $1.20 \times V_{PE}^2$. In this case, no optimization of the distance between the end of the tip of the robots' arm and the bottom surface is required.

In this second embodiment, prior to step a) of the first sequence, the at least one well on which step a) will be carried out is preferably free from solution of polyelectrolyte (or more generally, free of any solution, i.e. empty). The situation is thus different than the one when the first embodiment of the method is carried out and wherein, prior to step a) of the first sequence, the at least one well on which step a) will be carried out comprises a solution of the second polyelectrolyte $PE^2$.

This high spatial homogeneity of the obtained polyelectrolyte multilayer film enables to perform cell culture assays in optimized conditions. Of special importance for biomedical applications is the control of the homogeneity of the surface which can affect biological activity. These films can contain bioactive molecules and trigger controlled cellular adhesion and differentiation.

Moreover, building films directly at the bottom of multiple-well cell culture plates is of particularly interest, since this enables to combine in situ film characterization methods and high throughput cellular assays.

Notably, absorbance, fluorescence or even luminescence measurements can be done in routine using microplate readers.

In addition, provided that the culture plate is carefully chosen, it is also possible to simultaneously perform optical imaging at various resolutions, provided that the bottom of the plate is optically transparent and sufficiently thin to be compatible with high resolution objectives (×63 or above). The 96-well plate format seems especially suited for high throughput screening of surface coatings that contain expensive molecules, such as drugs, peptides or growth factors, since it enables to use low volumes of bioactive molecules, a low number of cells, and to perform in situ imaging of biomolecules and cells. The 96-well plate format is also particularly advantageous since it can be combined with high throughput optical and spectroscopic analysis. Notably, a 96 well plate with a thin bottom—around 180 µm—can be analyzed using a fluorescence/absorbance microplate readers as well as imaged under a fluorescence microscope at high resolution (63× objective or higher).

Bioactivity of the films can be achieved by their functionalization by inserting peptides associated to polyelectrolytes or through the embedding of proteins.

Accordingly, the method can comprise, after the n sequences, a step e') of robotic deposit of a volume $V_{PE}^3$ of a solution of a third polyelectrolyte $PE^3$ on said bottom surface, wherein:
  polyelectrolyte $PE^3$ is linked to at least a peptide, and
  the third polyelectrolyte $PE^3$ is a cationic polymer comprising amino groups when $PE^2$ is an anionic polymer, or $PE^3$ is an anionic polymer when $PE^2$ is a cationic polymer comprising amino groups.

Preferably, the peptide is RGD. Most preferably, the polyelectrolyte $PE^3$ is PGA-RGD.

Besides, in the embodiment wherein the anionic polymer comprises carboxylic groups, the method can comprise, after the n sequences, the following steps:
e) reacting said amino and carboxylic groups in the presence of a coupling agent, so as to form amide bonds and to cross-link the polyelectrolyte multilayer film, then
f) treating said cross-linked polyelectrolyte multilayer film with a protein containing solution, preferably with a growth factor type protein containing solution, so as to incorporate said protein on and inside said cross-linked polyelectrolyte multilayer film.

The coupling agent enables the formation of amide bonds (or derivatives thereof) between the carboxylic and amino groups of the polyelectrolyte multilayer. The coupling agent can act as a catalyst, which can be removed thereafter, or as a reactant, which creates a spacer (or a link) between the formed amide bonds. For example, the coupling agent is a carbodiimide compound, such as 1-ethyl-3-(3-dimethylaminopropyl) carbodiimide (EDC), optionally in the presence of N-hydroxysuccinimide compounds, such as N-hydroxysulfo succinimide, more preferably N-hydroxysulfo succinimide para-nitrophenol, or dimethylaminopyridine.

Step e) is preferably performed in a water soluble solution, more preferably in an aqueous solution, for example in a salt free solution or in an aqueous solution containing salts, such KCl, NaCl, or any kind of buffer such as Mes, Tris, Hepes, or phosphate buffers. Step e) is preferably carried out at a pH ranging from 4 to 6.

The degree of crosslinking can also be controlled by varying the concentration of the coupling agent in the solution.

Step f) is preferably carried out at a pH ranging from 2 to 9, more preferably from 2 to 5.5.

The protein containing solution is preferably a buffer, such as Mes buffer, preferably a solution with a low ionic strength, more preferably a buffer without any salt, such as HCl (for instance HCl at 1 mM).

Among the growth factor proteins that may be used, can be cited in particular those that are useful for therapeutic applications and/or for cell biology applications. As examples of growth factors that may be incorporated in films according to the invention are all bone morphogenetic proteins (BMPs), epidermal growth factors (EGF), erythropoietin (EPO), all fibroblast growth factors (FGF), granulocyte-colony stimulating factor (G-CSF), granulocyte-macrophage colony stimulating factor (GM-CSF), growth differentiation factor 5 and 9 (GDF5, GDF9), hepatocyte growth factor (HGF), hepatoma derived growth factor (HDGF), insulin-like growth factor (IGF), myostatin (GDF-8), nerve growth factor (NGF) and other neurotrophins, platelet-derived growth factor (PDGF), thrombopoietin (TPO), transforming growth factors, stromal cell-derived factor-1 (SDF-1) and vascular endothelial growth factor (VEGF), brain derived neuronal growth factor (BDNF).

Among the growth factor proteins, the transforming growth factor (TGF) family is a category of choice as this family plays an essential role e.g. in bone formation through the regulation of osteoprogenitor and osteoblast proliferation and differentiation. Bone morphogenetic protein 2 (BMP-2), a member of the TGF family, stimulates in particular the differentiation of myoblast cells toward an osteoblastic lineage; and its recombinant human form rhBMP-2 is more effective when delivered associated with a biological material such as a polymer.

The protein used at step f) can be a growth factor type protein, and preferably a transforming growth factor. More particularly, the growth factor is the bone morphogenetic protein 2 (BMP2) or the bone morphogenetic protein 7 (BMP-7), the stromal cell-derived factor-1 (SDF-I), or chimera 1 or chimera 2. The growth factor can be prepared by various methods, including biological or chemical methods. The recombinant form is a particular embodiment. The chemical method implements generally automated peptide synthesizer. For instance, wild type SDF-I can be synthesized by the Merrifield solid-phase method on a fully automated peptide synthesizer using fluorenylmethyloxycarbonyl (Fmoc) chemistry.

The method can comprise, between steps e) and f) or after step f), a step g) of drying the polyelectrolyte multilayer film. This step is advantageous to store the multiwell plate, and to transport it. The polyelectrolyte multilayer film can advantageously be rehydrated just before use.

According to a second object, the invention concerns the multiwell plate obtainable according to the method described above. This multiwell plate comprises at least one well, the bottom surface of which is coated by the polyelectrolyte multilayer film.

This multiwell plate is characterized in that said polyelectrolyte multilayer film has a high spatial homogeneity. This spatial homogeneity can easily be assessed, for example by the procedures and parameters defined in the examples hereafter (notably SD and CV).

The protein loaded crosslinked polyelectrolyte multilayer films obtained at the end of step f) are particularly useful when they are in contact with various cell types, such as myoblast and osteoblast precursors, the cells can adhere, proliferate and optionally differentiate in a very efficient manner. Advantageously, the cell adhesion and spreading on the obtained polyelectrolyte multilayer film is homogeneous. Cells distribute homogeneously on the entire surface of the well and only one population of well spread cells is observed. On the contrary, when the polyelectrolyte multilayer film is heterogeneous, the cell adhesion and spreading differs depending on the spatial position inside the well: typically, the cells are numerous and well spread at the center of the well, but there are both less cells and less spread cells toward the border of the well. Thus, a heterogeneous film leads to several distinct cell populations within the same well and leads to a spatial heterogeneity in cell adhesion and spreading. A homogeneous polyelectrolyte multilayer film as obtained by the method according to the invention is thus interesting for cell culture. Accordingly, according to a third object, the invention concerns the use of the multiwell plate for cell culture.

The following figures and examples illustrate the invention, but should not be regarded as limiting the scope of the application.

FIGURES

FIG. 1. Schematic of the layer-by-layer deposit at high throughput in multiple well cell culture plates. Working principle of process when the tilting embodiment is operated. The plate is tilted during all the deposit and aspiration steps in all four major deposit and rinsing steps: polycation and its rinsing, polyanion and its rinsing.

Figure 2:
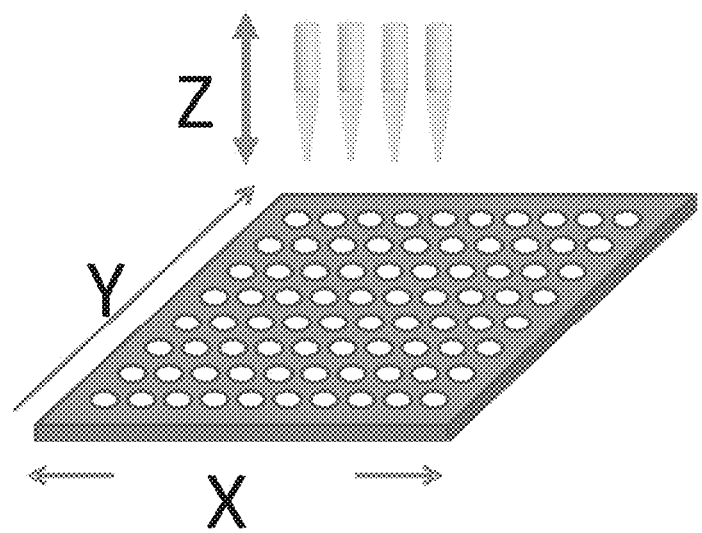

FIG. 2: Illustration of a multiwellplate and definition of the (X, Y, Z) coordinates, the (X,Y) coordinates of each well center being known for commercially available cell culture plates; Z0, the initial position of the tip during the dispense of solutions, needs to be defined by the user.

Figure 3:
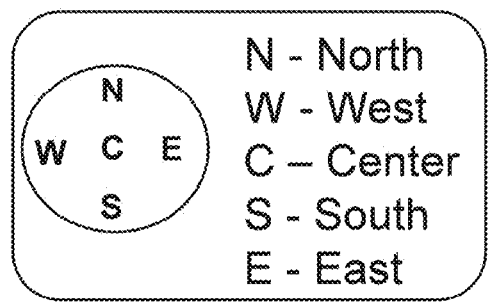

FIG. 3: Definition of the 4 pole positions (N, W, E, S) and center position (C) that are selected to assess the film thickness homogeneity inside each well. The imaging process of each of the 5 positions in each individual well was automatized using a custom-made macro using the confocal microscope software.

Figure 4:
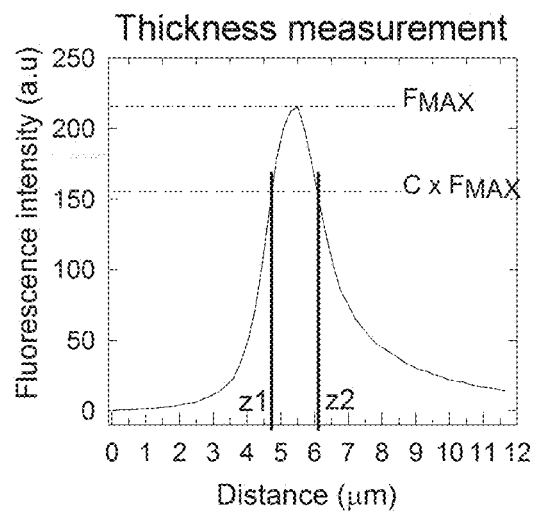

FIG. 4: Fluorescence intensity acquired via high resolution imaging in function of the distance Z from the bottom surface of the well. The film thickness h=Z2−Z1 was measured using a custom-made macro using Image J.

Figure 5:
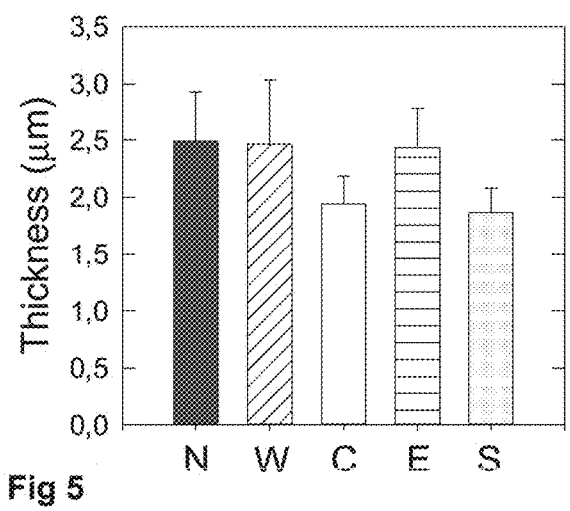

FIG. 5: Film thickness measured at the different pole positions (N, W, C, E, S) for each well in the case of hand-made films using a multichannel pipette (comparative example). The mean+Standard deviation (mean±SD) of hN, hW, hC, hE, and hS, respectively (for m=48 wells) are plotted for each position.

Figure 6:
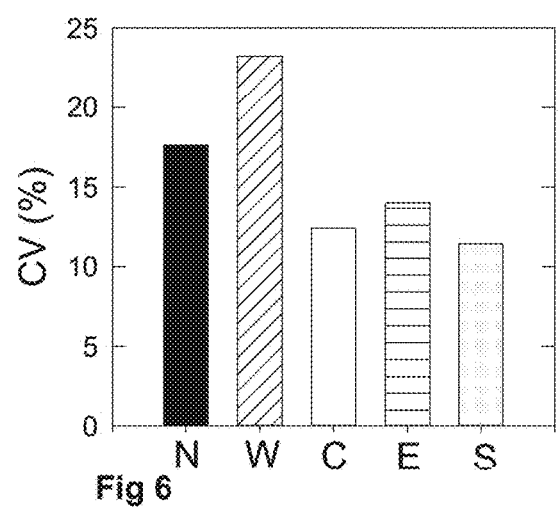

FIG. 6: CV (%) measured at the different pole positions (N, W, C, E, S) for each well in the case of hand-made films using a multichannel pipette (comparative example).

Figure 7:
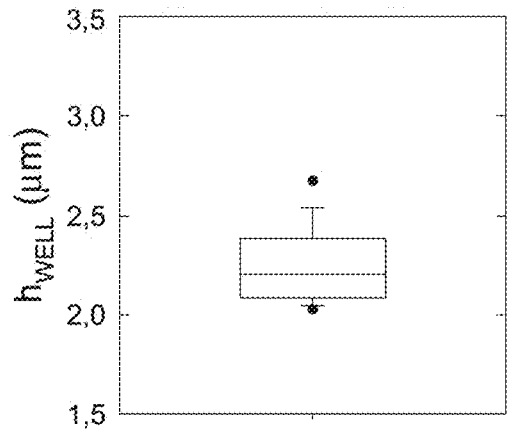

FIG. 7: Box plot of the mean thickness per well (hWELL) over m independent wells in the case of hand-made films using a multichannel pipette (comparative example).

Figure 8:
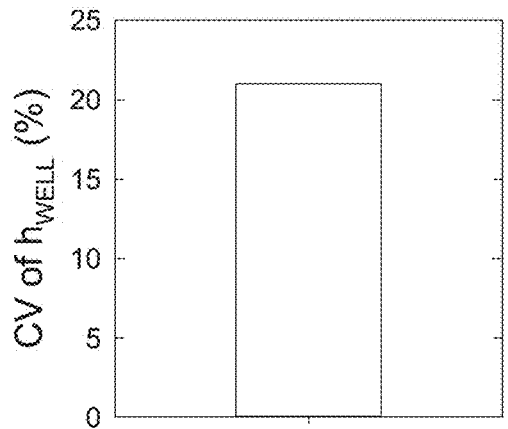

FIG. 8: CV of hWELL (with m=48 wells) in the case of hand-made films using a multichannel pipette (comparative example).

For FIGS. 5 to 8, data ware pooled for two independent experiments, each with 24 wells per multiwell plate (m=48 wells in total).

Figure 9:
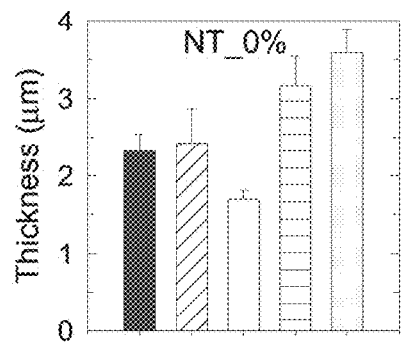

FIG. 9: Film thickness (µm)±SD measured at the different pole positions (N, W, C, E, S) for each well in the case of robot-made films for the condition NT_0% of example 1.

Figure 10:
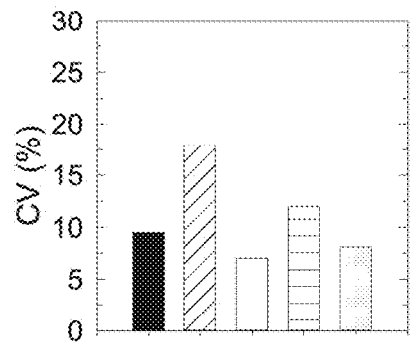

FIG. 10: CV (%) measured at the different pole positions (N, W, C, E, S) for each well in the case of robot-made films for the condition NT_0% of example 1.

Figure 11:
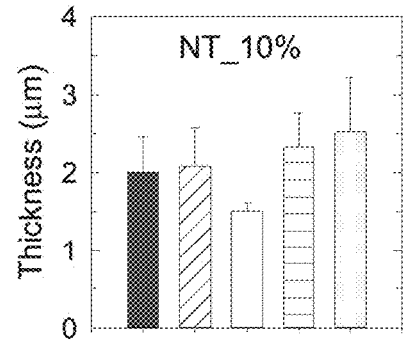

FIG. 11: Film thickness (µm)±SD measured at the different pole positions (N, W, C, E, S) for each well in the case of robot-made films for the condition NT_10% of example 1.

Figure 12:
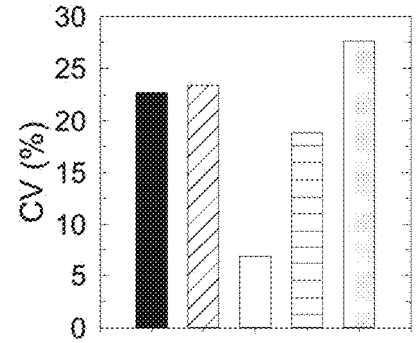

FIG. 12: CV (%) measured at the different pole positions (N, W, C, E, S) for each well in the case of robot-made films for the condition NT_10% of example 1.

Figure 13:
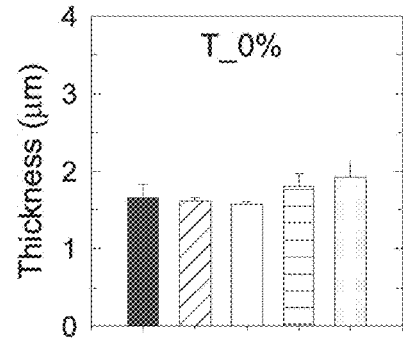

FIG. 13: Film thickness (µm)±SD measured at the different pole positions (N, W, C, E, S) for each well in the case of robot-made films for the condition T_0% of example 1.

Figure 14:
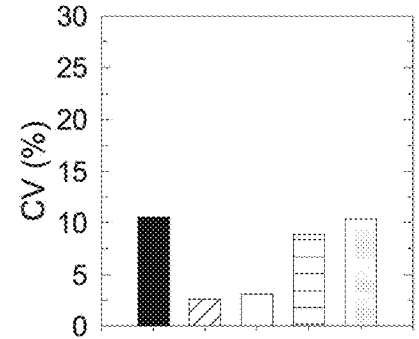

FIG. 14: CV (%) measured at the different pole positions (N, W, C, E, S) for each well in the case of robot-made films for the condition T_0% of example 1.

Figure 15:
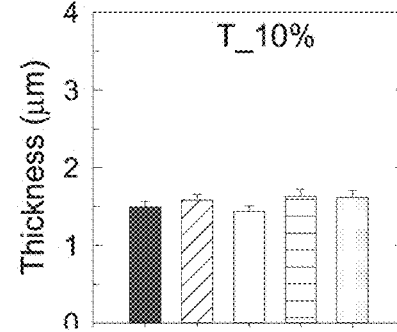

FIG. 15: Film thickness (µm)±SD measured at the different pole positions (N, W, C, E, S) for each well in the case of robot-made films for the condition T_10% of example 1.

Figure 16:
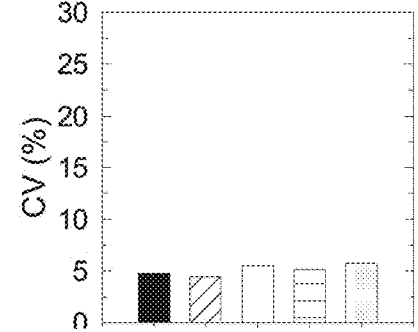

FIG. 16: CV (%) measured at the different pole positions (N, W, C, E, S) for each well in the case of robot-made films for the condition T_10% of example 1.

Figure 17:
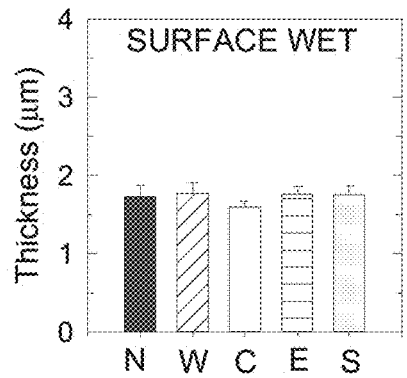

FIG. 17: Film thickness (µm)±SD measured at the different pole positions (N, W, C, E, S) for each well in the case of robot-made films for the condition surface wet of example 1.

Figure 18:
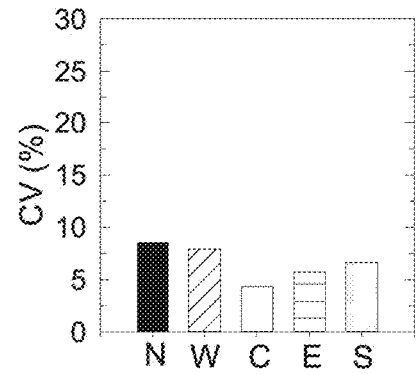

FIG. 18: CV (%) measured at the different pole positions (N, W, C, E, S) for each well in the case of robot-made films for the condition surface wet of example 1.

For FIGS. 9 to 18, data are mean±SD and CV for 9 wells in total per condition, from two independent experiments.

Figure 19:
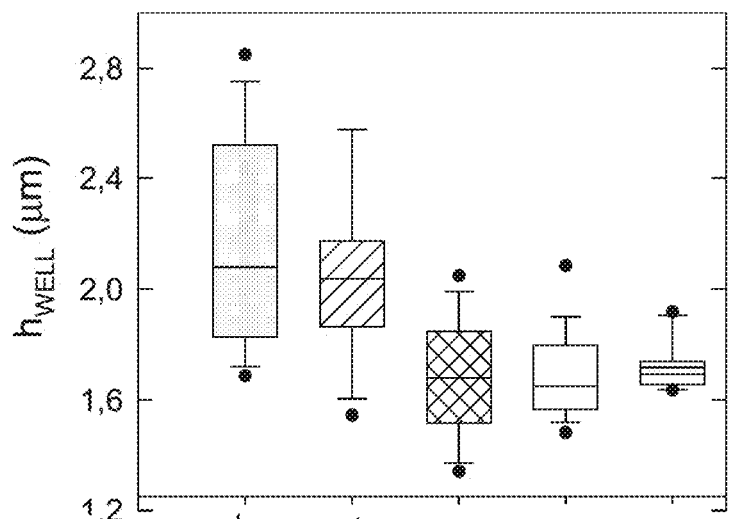
Figure 20:
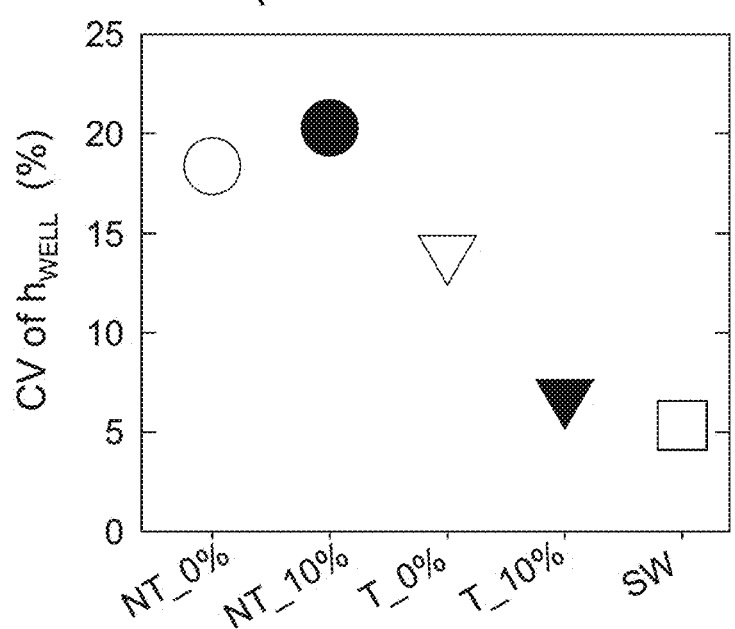
Figures 21, 22, 23, 24, 25:
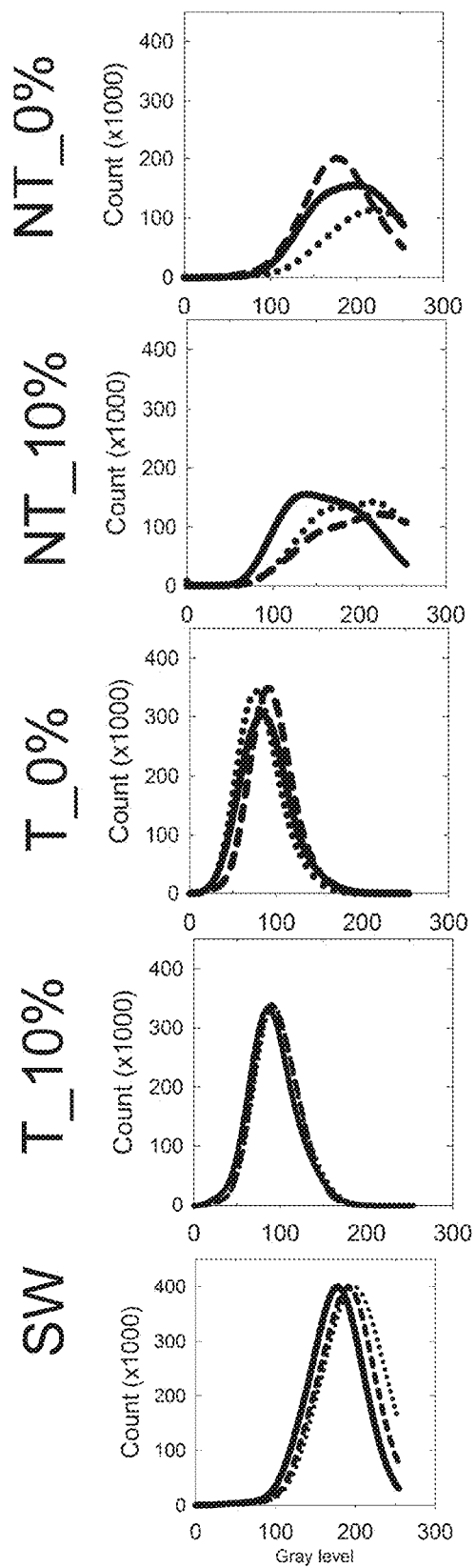

FIG. 19: Mean thickness per well (hWELL) for (PLL/HA) 12 film made in 96-well plates using the robotic arm. Mean thickness per well was calculated, for each individual microwell, as the mean of the 5 positions. All mean thickness measurements were plotted as box plot for each of the 5 experimental conditions. Data are: from 33 microwells (from 3 independent experiments) for NT conditions; for 81 wells (from 4 independent experiments) for T conditions, and from 12 wells for Surface Wet conditions (Example 1) Data representation: Data are represented as box plots showing 1st quartile, median, 3rd quartile, the limits being 10 and 90% and the extreme values 5 and 95%, respectively FIG. 20: CV for (PLL/HA) 12 film made in 96-well plates using the robotic arm corresponding to the Mean thickness per well illustrated in FIG. 19 (example 1).

FIGS. 21 to 25: For each experimental condition (FIG. 21: NT_0%—FIG. 22: NT_10%—FIG. 23: T_0%—FIG. 24: T_10%—FIG. 25: surface wet), 3 representative curves of the fluorescence intensities (acquired using the tile scan option of the confocal microscope) of all pixels in each well are shown (continuous, dashed and dotted black lines) (example 1). The standard deviation of their height is given in Table 2.

FIGS. 26 to 29: Thickness measurements at the five pole positions (N, W, C, E, S) and at different distances (Z-step) between the end of the tip and the bottom surface for each of the 4 experimental positions (FIG. 26: NT_0%—FIG. 27: NT_10%—FIG. 28: T_0%—FIG. 29: T_10%). The end of the tip was positioned at 4 different heights above the bottom of the microplate, from Z0=+0.1 to +1 mm by steps of +0.3 mm. (eg +0.1; +0.4; +0.7 and +1 mm above the bottom of the well (n=6 well per condition). Each box plot represents a total of 30 thickness measurements on 6 independent wells at 5 positions inside each well.

Figure 30:
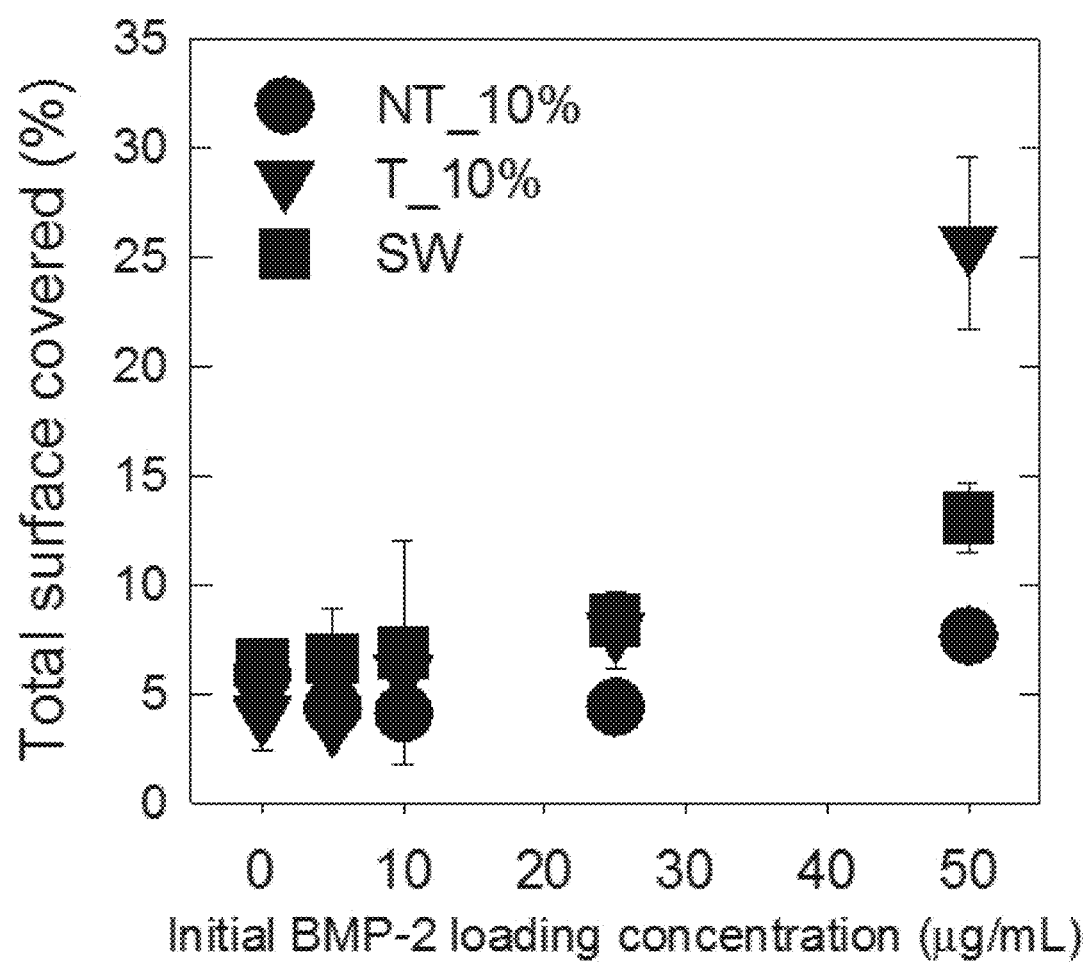

FIG. 30: % of surface area covered (calculated from tile scan images of the microwells) by C2C12 cells for the three experimental conditions as a function of the BMP-2 initial concentration of loading. Data are mean±SD of at least 10 wells (example 3)

Figure 31:
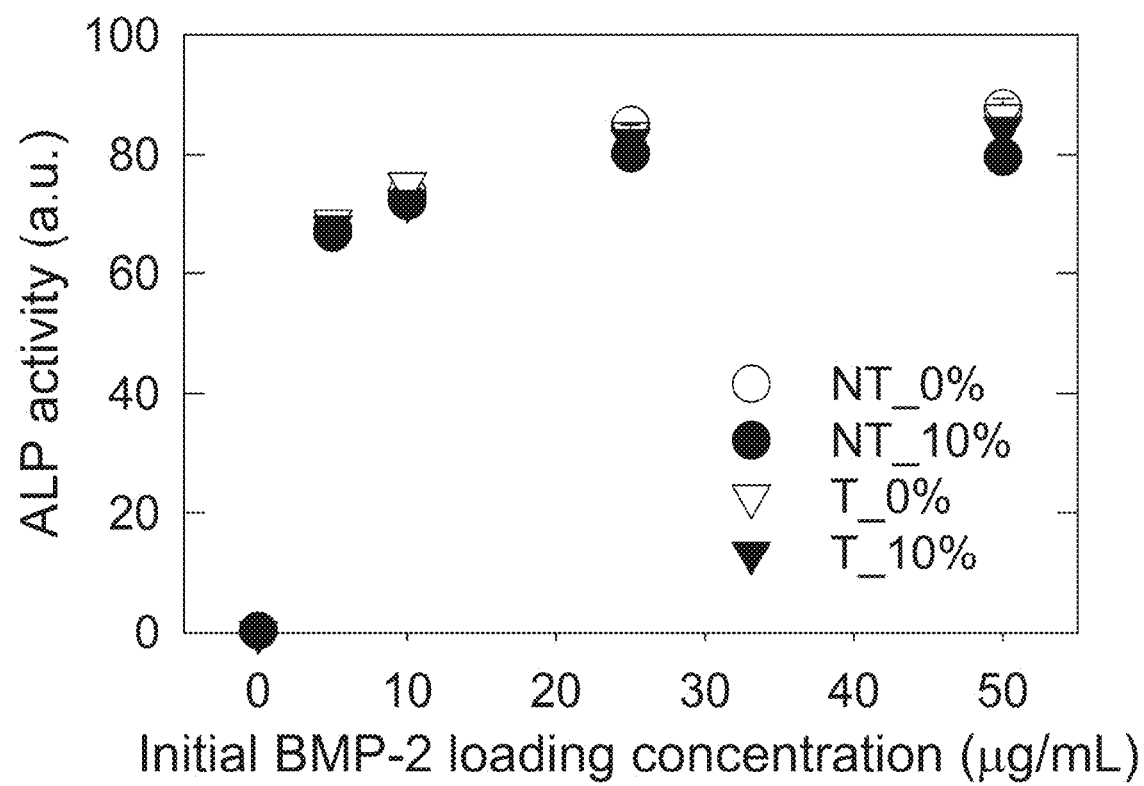

FIG. 31: ALP activity (a.u.) by the cells for the four experimental conditions as a function of the BMP-2 initial concentration of loading (example 3). Bioactivity of matrix-bound BMP-2 on C2C12 cells. (PLL/HA) films built using the robotic arm were crosslinked (with EDC30), post-loaded with BMP-2 at 5, 10, 25 and 50 µg/mL were assessed for their bioactivity. C2C12 cells plated at 5000 cells/well in growth medium were stained for ALP after 3 days of culture. (Example 3)

Figure 32:
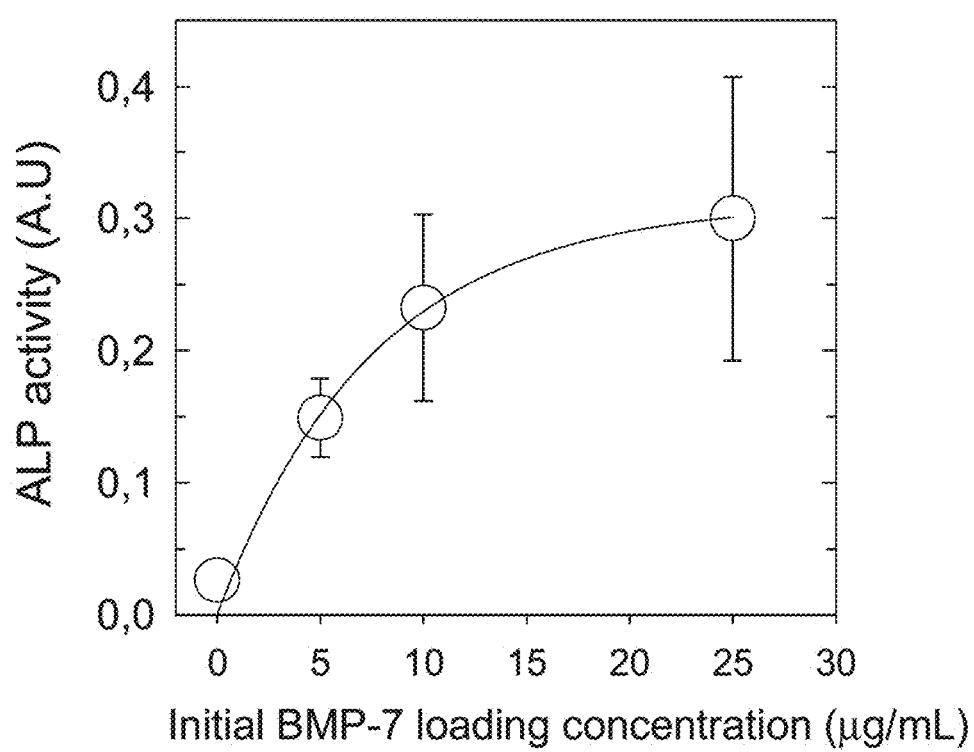

FIG. 32: ALP activity (a.u.) of stem cells for the T_10% condition as a function of the BMP-7 initial concentration of loading. Bioactivity of matrix-bound BMP-7 on D1 stem cells. Matrix-bound BMP-7 was loaded on crosslinked (PLUHA)12 films (crosslinked with EDC10), which were prepared using the robotic arm in the T_10% condition. D1 murine mesenchymal stem cells were plated in each microwell and cultured up to 2 days in GM, before being switch in DM for 7 additional days. ALP activity was quantified by enzymatic assay. 4 increasing BMP-7 loading concentrations from 2.5 to 50 µg/mL were tested in comparison to the film in the absence of BMP-7. ALP expression at day 3 is plotted as a function of the BMP-7 loaded dose in the polyelectrolyte films. Data are mean±SD of three independent wells for each experimental condition.

Figure 33:
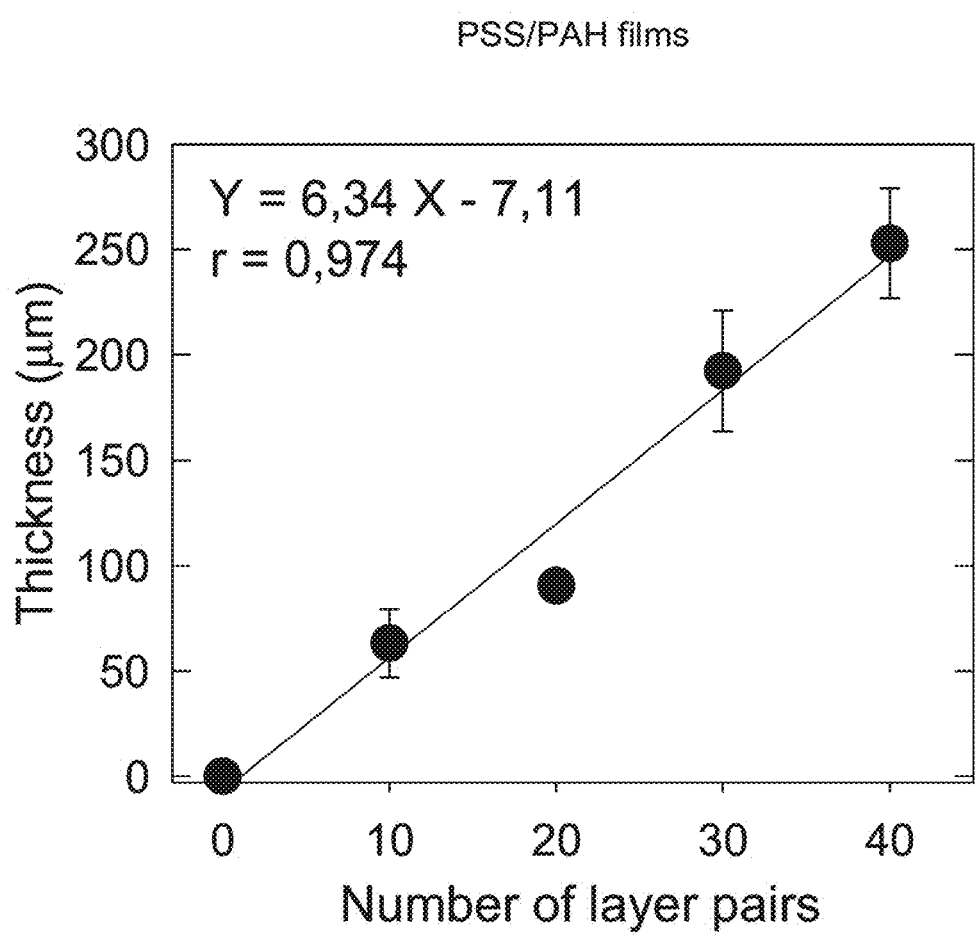

FIG. 33: Film thickness of (PSS/PAH) polyelectrolyte films as a function of n (number of layer pairs) (PSS/PAH) films containing an increasing number of layer pairs from 10 to 40 were deposited using the robotic arm with the condition T_10% on a silicon substrate using PDMS microwells. After film deposit, the PDMS wells were removed and the samples were probed by AFM. Film thickness are measured after scratching of the films. Data are mean±SD of 25 measurements (5 independent measurement per sample, 5 samples for each experimental condition). The linear fit of the data (Y=6.34X−7.11, R=0.974) confirms the linear growth of these films.

Figure 34:
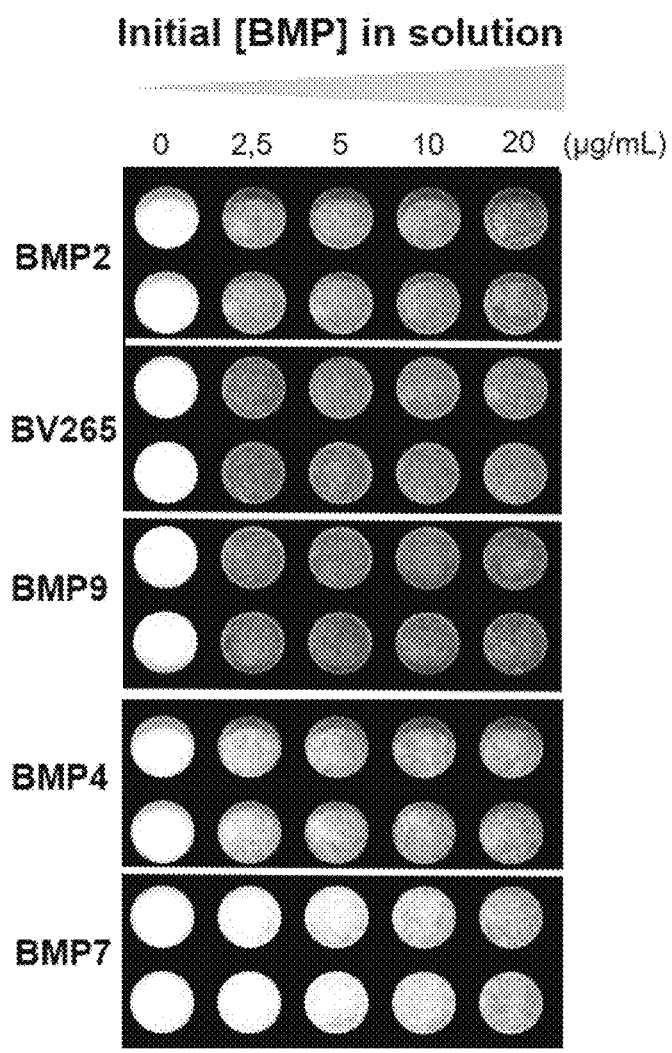

FIG. 34. Bioactivity of matrix-bound BMPs on the BMP responsive skeletal myoblasts (C2C12 cells) assessed by visual observations using a scanner. ALP activity of C2C12 myoblasts cultured for 3 days on BMP-loaded films (crosslinked to EDC70) was visualized at high throughput for each single well by the intensity of the staining. 5 different BMPs were studied (BMP-2, BMP-4, BMP-7, BMP-9, and BV265) and 4 different BMPs loaded quantities (initial BMP concentration in solution from 2.5 to 20 µg/mL).

Figure 35:
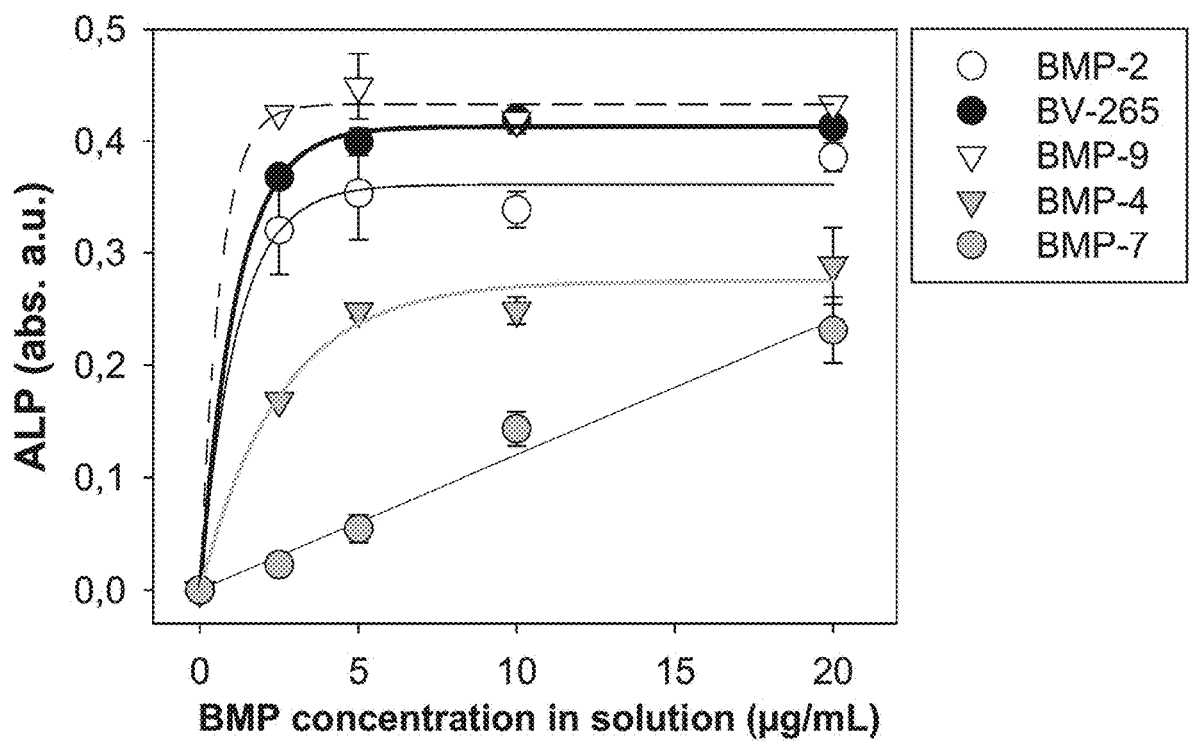

FIG. 35: Bioactivity of matrix-bound BMPs on the BMP responsive skeletal myoblasts (C2C12 cells). ALP activity (a.u.) was measured as a function of the initial concentration of BMP in solution during the loading phase in the biomimetic films. Matrix-bound BMPs were loaded on crosslinked (PLUHA) 12 films (crosslinked with EDC70), which were prepared using the robotic arm in the T_10% condition. C2C12 myoblasts were plated in each microwell and cultured for 3 days in GM. ALP activity was quantified measuring the absorbance at 570 nm using a Tecan Infinite 1000 microplate reader in a multiple reading mode (mean value of 76 different positions in each single microwell). For each BMP (BMP-2, BMP-4, BMP-7, BMP-9, and BV265, 4 increasing BMPs loading concentrations from 2.5 to 20 µg/mL were tested in comparison to the film in the absence of BMPs. ALP expression at day 3 is plotted as a function of the initial BMPs concentration in solution. Data are mean±SD of two independent wells for each experimental condition.

Figure 36:
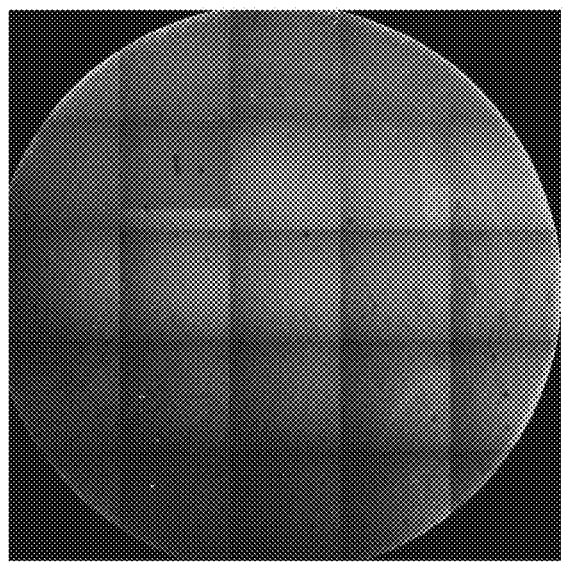

FIG. 36. Tile scan imaging of a single microwell (6.4 mm in diameter) coated with a PGA/PLL film made of 5 layer pairs. The film was visualized by using PLL-FITC.

Figure 37:
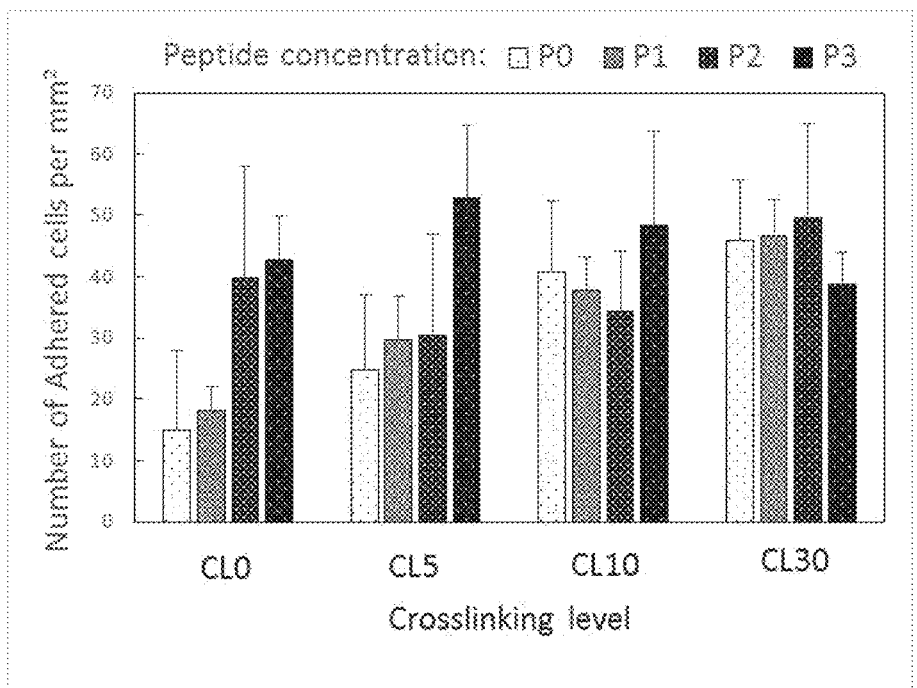

FIG. 37. Number of C2C12 myoblast cells (per mm2) adhering on the on the PGA-peptide ending biomimetic films after 1 H of culture in a serum-free medium. 4 different conditions of film crosslinking were studied (CL0, CL5, CL10, CL30) and four different PGA/PGA-RGD peptide were studied (no peptide, ratio 2/1 ratio 1/2 and only PGA-peptide). Data are mean+SD of three independent well for each experimental conditions.

Figure 38:
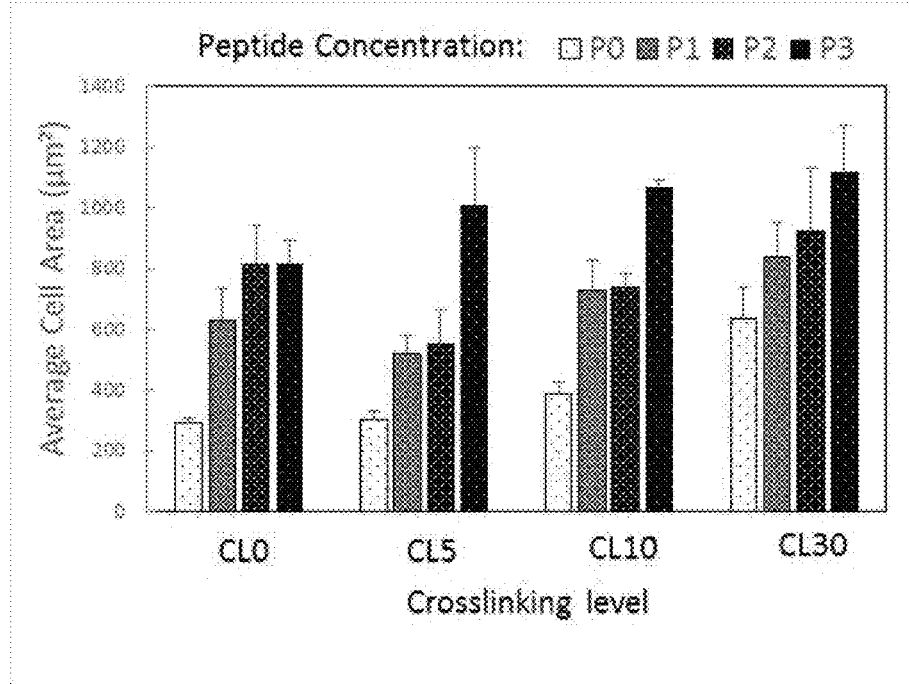

FIG. 38. Quantification of the myoblast cell spreading area (same experimental conditions as for figure XY. Cell spreading area was automatically quantified using a custom-made macro using Image J ton calculate the cell area covered by the cells and deduce the mean cell spreading area.

EXAMPLES

Polyelectrolytes

Different types of polyelectrolytes were used for the film buildup: Poly(L-lysine) hydrobromide (PLL, Sigma, Aldrich, St Quentin Fallavier, France), Poly(allylamine hydrochloride), chitosan (CHI, FMC Biopolymers) and poly (ethylene imine) (PEI, Sigma Aldrich, France) as polycations; Hyaluronic acid (HA, Lifecore Biomedical, USA), Polystyrene sulfonate (PSS) and poly(L-glutamic acid) (PGA, both from Sigma Aldrich, France) as polyanions. PGA was grafted to a RGD containing peptide as described in Picart et al, *Adv. Funct. Mat* 2005:15, 83-94)

Four different polycation/polyanion couples were selected:
- the (PLL/HA) films is a model system of exponentially growing films. For films made of 12 layer pairs, the thickness should be around 1.5 to 2 µm, i.e. close to the resolution limit of detection by confocal laser scanning microscopy (CLSM).
- (PSS/PAH) films are another model system known to growth linearly with the number of deposited layers.
- (CHI/PGA) films were chosen as third polyelectrolyte films to show the potentiality of the robot with other polyelectrolytes.
- (PLL/PGA) films were chosen as fourth polyelectrolyte films to show the potentiality of the robot to deposit other polyanions and to do high throughput screening of cell adhesion and spreading on films that were prepared using the robot and a film having as final layer a mixture of PGA and PGA-RGD.

Buffers for Film Buildup

For (PLL/HA) film buildup, PLL (0.5 mg/mL), HA (1 mg/mL) and PEI (2 mg/mL) were dissolved in a HEPES-NaCl buffer (20 mM Hepes at pH 7.4, 0.15 M NaCl). In order to improve film adsorption to the substrates, a first layer of PEI was deposited, followed by an HA layer. Afterwards, the cyclic deposit method of polycation (PLL) and polyanion (HA) intercalated with rinsing steps started until the desired number of layers was reached. All rinsing steps during film buildup were performed with 0.15 M NaCl at pH 6.5.

For (PLL/PGA) film buildup, PLL and PGA were dissolved at 1 mg/mL in the Hepes-NaCl buffer.

For (PSS/PAH) film buildup, PAH and PSS were dissolved at 5 mg/mL in a Tris-NaCl buffer (pH 7.4 containing ×0.15 M of NaCl⁻

For CHI/PGA film buildup, CHI and PGA were dissolved in a 0.1 M sodium acetate buffer at pH 5 containing 0.15 M NaCl. For imaging, CHI was fluorescently labelled with Alexa Fluor 568 (Invitrogen, Amine Reactive Probe) in accordance with manufacturer's protocol excepting a 2 h reaction at pH 6.0. Product purification and removal of unbound dyes was carried out using a Sephadex G-25 size exclusion column (PD-10, Amersham Bioscience, Sweden). Films made of 12 layer pairs were imaged in air using the Zeiss LSM 700 confocal microscope with a 10× objective.

Comparative Example

Film Deposit by Hand Using a Multiple-Channel Pipette

LbL films were built by hand in 96-well cell culture plates using a multichannel micropipette (Eppendorf Research® pro 300, Germany), typically a channel with 8 tips. The polyelectrolytes were dispensed in each well and incubated for 8 min. Polycation and polyanion dispense was intercalated with 2 rinsing steps of 2 min. The liquid was dispensed carefully by tiling of the plate. It was thrown away by reversing the plate upside down. (PLL/HA) films made of 12 pairs of layers were manually deposited in 24 wells using a 8-arm multichannel pipette. PLL-FITC was used to stain the film.

First, this procedure is tedious and requires the experimentalist to be highly focused for several hours. Besides, it is time consuming since the total time needed for film deposit may be very long: it is proportional to the number of deposited layer pairs n. For instance, it takes up to two full days of work to manually prepare a film made of 24 pairs of layers.

In addition, polyelectrolyte film deposition by hand reveals to be highly heterogeneous inside a single well, as can be observed on the film thickness analysis at the different pole positions (FIGS. 5 to 8). The coefficient of variation for the different pole positions varied between 10 to 23% in each specific location, and the mean thickness per well varied of the order of 20% between independent wells (for two independent experiments pooled together). Without wishing to be bound by a theory, the inventors assumed that these spatial heterogeneities may originate from capillary effects, which are known to be important at such length scale.

Example 1

Automated (PLL/HA) Film Buildup Using a Liquid Handling Machine

A large set of in situ physico-chemical characterization and biological studies was performed in the same plate: i) LbL deposit (example 1), ii) characterization of the LbL film homogeneity in situ (example 1), iii) loading of bioactive proteins and its characterization (example 3), iv) assessment of the bioactivity of the protein-loaded LbL films on cell cultures in situ in microplates: short term adhesion and ALP activity were quantified at high throughput using optical microscopy and spectroscopy (example 3).

Automated Film Buildup Using a Liquid Handling Machine

LbL films were directly deposited in 96-wells cell culture plates (Reference 655986, Greiner bio-one, Germany) for subsequent characterization in situ (in liquid or air) by confocal microscopy and using a fluorescence/absorbance microplate reader. A protocol was developed to deposit layer-by-layer films at high-throughput in multiple-well plates using an automated liquid handling machine (TECAN Freedom EVO® 100) (FIG. 1).

The film buildup with this equipment consisted in sequences of polycation and polyanion dispense intercalated with rinsing steps. The principle consisted in using a liquid handling pipetting arm. This liquid handling arm pipetted the liquids in their respective reservoirs and dispensed them in selected wells of the multiple-well plate (FIG. 2). The trough containing the polyelectrolytes and the rinsing solution were deposited on the worktable. Three through were used: one for the polycation, one for the polyanion and one for the rinsing solutions (two in case the rinsing solutions would be different) and a trash. The multiple-well culture plates was/were deposited on the worktable.

We created an option for tilting the plate during dispense and aspiration steps (FIG. 1), using a commercially available tilting plate carrier: the multiple-well plate can be tilted at an angle α that is defined by the user and can typically vary between 5 and 20 degrees, and was 20 degrees in the examples hereafter. This condition will be named hereafter "Tilting" (T) versus "Non Tilting" (NT) for the standard position of the plate on the worktable ($\alpha$=0 degree).

First, using a custom-made macro with the robot software, we defined the number of wells and specific positions where we wanted the layer-by-layer film to be deposited.

A sequence, i.e. a pair of layers, was made of the following steps:

the liquid handling arm aspirated the polyelectrolyte from the trough and dispense it in the selected wells (typically 50 µL) using a tip (FIG. 2), this step being called "the dispense", incubation time in the polyelectrolyte solution of 6 min, the liquid in each well was aspirated back and dispensed in the trash. During this step, it is possible to add an additional aspiration volume.

In the examples below, the defined volume is the additional aspiration volume, defined as a % of excess volume with respect to the volume initially deposited in that specific well (0, 5, 10, 15 or 20%, respectively corresponding to $1.00 \times V_{aspPE}$, $1.05 \times V_{aspPE}$, $1.15 \times V_{aspPE}$ and $1.20 \times V_{aspPE}$, as defined above (PE being either $PE^1$ or $PE^2$)); for example: if the additional aspiration is fixed to 10%, the robot will aspirate back 55 µL for an initial dispensed volume of 50 µL.

2 rinsing steps were done following the same procedure, except that the liquid was then aspirated from the rinsing trough (rinsing volume of 80 µL).

the liquid arm aspirated the oppositely-charged polyelectrolyte (typically 50 µL) from the trough and dispensed it in the selected wells, incubation time of the oppositely-charged polyelectrolyte of 6 min.

the polyelectrolyte in each well was aspirated back and dispensed in the trash.

x rinsing steps (typically 2) of the oppositely-charged polyelectrolytes (typically 80 µL) were done following the same procedure, except that the liquid was then aspirated from the rinsing trough (rinsing volume of 80 µL).

For more precision in the pipetting, the dispenses may be achieved with the most appropriate pipetting tip, such as 200 µL. The aspiration may be done with a 1 mL tip.

This sequence was repeated n times to build a layer-by-layer film made of n layer pairs.

Experimental Conditions

We compared five experimental conditions:

By controlling the tilting of the microplate (Non Tilting or Tilting condition with an inclination angle $\alpha$ of 20° relative to the horizontal plane, respectively "NT" or "T") and the additional aspiration volume (fixed to 0% or 10%): There are four conditions in total named hereafter: NT_0%; NT_10%; T_0%; T_10%.

The 5th and last condition is a Non tilting/0% additional aspiration (i.e. ($V_{aspPE}^1 = V_{PE}^1$ and $V_{aspPE}^2 = V_{PE}^2$) but with a permanent excess volume during the buildup method (i.e. $V^{wet}$). We name it hereafter "Surface Wet" condition.

For this condition, a volume of $PE^1$ polyelectrolyte solution was dispensed inside each well at the very beginning of the experiment (for a well of a 96-well plate, this volume was set to 30 µL). This allows a constant volume of solution to be left inside each well, in order to ensure that the surface always remains covered by the liquid. By doing so, we aim to avoid local differences in the height of the liquid film above the polyelectrolyte film.

Pipetting Speed

The pipetting speed can be controlled by the user in the working range of the robotic arm. Typical pipetting speed were set to 400-800 µL/s for the dispense step and 30-150 µL/s for the aspiration steps.

Characterization of Film Homogeneity Inside a Well (Tile Scans and Transverse Sections)

Provided that one of the film components is labelled with a fluorescent dye, it is possible to image the global film homogeneity inside a given well using a Tile scan option of a confocal microscope (Zeiss LSM 700, Le Peck, France) and a 10× objective. This option enables to automatically scan the well by acquiring subsets of images.

Film Thickness "h"

We used PLL-FITC for (PLL/HA) films and (CHI-FITC) for (CHI/PGA) films to visualize the films. In fact, for exponentially growing films, it is known that the last layer is able to diffuse within the whole film. Thus, the film thickness can be easily measured by measuring the thickness of the fluorescence band.

To assess the film homogeneity inside each well at high spatial resolution, we measured film thicknesses at five different positions inside each well (North, West, Center, East and South, respectively N, W, C, E, S, FIG. 3). The center was approximately the center of the well, as assessed by the user. The other poles were located at +2 mm from the center, respectively, in the X and Y directions. To measure film thickness at these positions (the total number of positions being equal to the total number of wells×5), we automated the acquisition of the transverse sections at 0.36 µm intervals using a 63× oil objective and a custom-made macro with Zen software (Zeiss). Then, each thickness was automatically deduced from the fluorescence intensity profile (FIG. 4), using a custom-made macro on Image J (NIH. Bethesda). A typical fluorescent intensity profile starts off at the noise level (close to 0), increases to a peak value as the focal plane goes deeper into the film, and then returns to the noise level. In brief, the maximum of intensity ($F_{MAX}$) was first determined. We applied a threshold coefficient C so that $I=C \times F_{MAX}$. We then deduced the Z position (Z1, Z2) at which this line intercepts the fluorescence intensity profile. The film thickness h can be easily deduced: h=Z2-Z1 (in µm). Of note, this macro was validated by comparing film thicknesses measured manually, by atomic force microscopy and by the macro on the same image.

The film thicknesses were determined at the different positions N, W, C, E, S inside each well and the corresponding thicknesses hN, hW, hC, hE and hS were determined.

Mean Thickness Per Well "hWELL"

The mean thickness per well hWELL was calculated as the sum of all 5 thickness measurements at the pole positions (N, W, E, S) and at the center (C), divided by 5. Thus, it was calculated using the formula:

$$h_{WELL} = \frac{(hN + hW + hC + hE + hS)}{5}$$

Mean Thickness of m Independent Wells "hMEAN"

hMEAN was calculated as:

$$hMEAN = \frac{\sum_{1}^{m} hWELL}{m}$$

Standard Deviation "SD" of the Mean Thickness Per Well (hWELL), for m Independent Wells
SD was calculated as:

$$SD = \sqrt{\frac{\sum_{i}^{m}(hWELLi - hMEAN)^n}{(m-1)}}$$

Coefficient of Variation "CV" of the Mean Thickness
The Coefficient of Variation (CV) of the mean thickness for each of the 5 positions or for each well was calculated by:

$$CV = \frac{SD}{hMEAN} \times 100$$

CV enables to compare samples independently of their absolute thickness values.

Film Deposit in PDMS Microwells on Silicon Wafers for Ex Situ Characterization

Film built on silicon wafers (2" diameter, Dow Corning, USA) were needed for ex-situ characterization using infrared spectroscopy, profilometry and AFM microscopy.

We designed a custom-made silicon substrate with polydimethylsiloxane (PDMS, Sylgard 184 kit, Dow Corning) wells of similar size than those of the 96-well plates. PDMS was mixed with curing agent (10:1) during 10 min and placed in a desiccator for 20 min to remove bubbles. Then, it was introduced in a mold, degassed again during 20 min and placed in the oven at 65° C. for at least 4 h, before being carefully removed from the mold and cut in rectangular pieces. Circular holes of the same diameter and position as in 96 well plates were made. Both silicon and PDMS substrates were UV treated (PSD-UV ozone cleaning system, Novascan Technologies) for 10 min to increase the bonding strength between them. Thereafter, the treated faces were set in contact, pressed to adhere and introduced in an oven at 100° C. for 1 h30 to be glued together. The (PSS/PAH) and (PLL/HA) polyelectrolyte films were then deposited using the robotic arm as described above.

For ex-situ film characterization an additional drying step was mandatory.

For (PLL/HA) films, the crosslinked films stored in Hepes-Nacl buffer were rinsed with MilliQ water and then dried.

For (PSS/PAH) films, the films were simply rinsed with MilliQ water and then dried. Film drying was done in an incubator for 2 h at 37° C. At the end of the procedure, the PDMS mold was removed and the films were kept at 4° C. Before each FTIR and profilometric analysis, the films were placed in an incubator at 37° C. for 1 h in order to eliminate any possible effect of humidity variation. Dry films were also characterized by AFM.

Ex Situ Analysis Using Infrared Spectroscopy, Profilometry and Atomic Force Microscopy FTIR Analysis Experiments were made using a Vertex 70 spectrophotometer (Bruker Optics Gmbh, Ettlingen, Germany) in the transmission mode using a sensitive MCT (Mercury-Cadmium-Telluride) detector. Prior to film analysis, a background signal was acquired after introducing a bare silicon substrate in the sample compartment using the transmission accessory. Dried films built on silicon substrate were placed in a sample holder and their spectra was acquired by summing 256 interferograms. Spectra analysis was made using OPUS Software v6.5 (Bruker, Germany), removing H2O and CO2 contributions and correcting the baseline manually, always choosing the same reference points in each spectrum. For each condition, a final spectrum is an average of 3 different spectra of the same sample (but from different wells).

Profilometry

Thickness measurements of films built on a silicon substrate were performed using a profilometer (Dektak XT, Bruker Corporation, USA). Five samples of each condition, corresponding to 5 different wells built at the same time, were scratched to create a physical step and three measurements per sample were acquired with the software Vision 64® (v 5.4, Bruker Corporation, USA). Scans of 30 s with a length of 1000 µm were performed with a stylus of 12.5 µm in radius and with a force set to 1 mg. Thus, film thickness for each condition was an average value of 15 measurements.

AFM

AFM images of the polyelectrolyte films deposited on silicon were obtained in tapping mode by means of a DI 3100 AFM (Veeco) with NanoScope IIIa controller using silicon cantilever (OMCL-AC240TS, Olympus). The film-coated substrates were washed in water and air-dried before observation. Substrate topographies were imaged with 512× 512 pixels at a frequency of 1 Hz.

Influence of the Tilting ("T")/Non Tilting ("NT"), of the Additional Aspiration and of the "Surface Wet" Condition on Film Homogeneity in a Single Well and Between Wells Film homogeneity inside each well was assessed at the 5 pole positions (FIGS. 9 to 18). The results are provided at tables 2 and 3 below.

TABLE 2

Experimental values measured for all the parameter studied for the 5 different experimental conditions.

| PARAMETER | NT_0% | NT_10% | T_0% | T_10% | SW |
|---|---|---|---|---|---|
| Mean ± SD of CVs of the 5 positions | 19.3 ± 9.8 | 20.6 ± 5.4 | 7.1 ± 3.9 | 5.1 ± 0.5 | 6.6 ± 1.6 |
| CV of (hWELL) (%) | 18.3 | 20.3 | 14 | 6.8 | 5.3 |
| Global Film Homogeneity (Tile scans) | 0.742 | 1.004 | 0.172 | 0.177 | 0.494 |
| Cell spreading (mm$^2$) for BMP50 | | 1200 ± 486 | | 1828 ± 697 | 1620 ± 512 |

TABLE 2-continued

Experimental values measured for all the parameter studied for the 5 different experimental conditions.

| PARAMETER | NT_0% | NT_10% | T_0% | T_10% | SW |
|---|---|---|---|---|---|
| Total surface covered (%) for BMP50 | | 7.6 ± 0.3 | | 25.6 ± 3.9 | 13.0 ± 1.6 |
| ALP bioactivity | 85 | 83 | 84 | 83 | 84 |

In order to facilitate comparison of the five conditions, based on the experimental values, a score was attributed for each criteria, the higher the score, the better the parameter. A total mean score was then calculated.

TABLE 3

Score for all the parameters studied for the 5 different experimental conditions.

| PARAMETER | NT_0% | NT_10% | T_0% | T_10% | SW |
|---|---|---|---|---|---|
| Mean ± SD of CVs of the 5 positions | 2 | 2 | 4 | 5 | 5 |
| CV of (hWELL) (%) | 2 | 2 | 3 | 5 | 5 |
| Global Film Homogeneity (Tile scans) | 2 | 1 | 5 | 5 | 3.5 |
| Cell spreading (mm²) for BMP50 | | 1.5 | | 5 | 4 |
| Total surface covered (%) for BMP50 | | 1.5 | | 5 | 3.5 |
| ALP bioactivity | 5 | 5 | 5 | 5 | 5 |
| TOTAL SCORE | 2.8 | 2.2 | 4.25 | 5 | 4.3 |

The ranking of table 3 gives the three first best conditions: T_10%>SW>T_0%. The NT_0% and NT_10% are very close and well below the others.

Accordingly, it appears both from the absolute thickness measurements (FIGS. 9, 11, 13, 15 and 17) as well as from the CV for each pole (FIGS. 10, 12, 14, 16 and 18) that:
 the "surface wet" condition (first embodiment describes above), and
 the conditions with tilting (second embodiment describe above),
  either with no additional aspiration ($V_{aspPE}^1 = V_{PE}^1$ and $V_{aspPE}^2 = V_{PE}^2$),
  or with 10% additional aspiration ($V_{aspPE}^1 = 1.10 V_{PE}^1$ and $V_{aspPE}^2 = 1.10 V_{PE}^2$), lead to more homogeneous films.

In addition, the mean thickness per well (FIG. 19) is also much less variable for the experiments with tilting, especially the condition with tilting and 10% addition aspiration, and for the surface wet condition.

CV values (FIG. 20) are systematically above 15% for the "non tilting" (NT) conditions, between 10 and 15% for the T_0% condition and less than 8% for both T_10% and for surface Wet.

A global view of the wells using PLL-FITC to visualize the films and the tile scan option of the confocal microscope software provided complimentary information on the global film homogeneity in each well. Three representative histogram of fluorescence intensities are plotted in FIGS. 21 to 25. The obtained images, as well as the histograms, clearly showed that the fluorescence distribution is more homogeneous in the T_0% (FIG. 23) and T_10% (FIG. 24) conditions and in the Surface Wet condition (FIG. 25) compared to the "non tilting" (NT) conditions.

Influence of the Positioning of the Pipetting Tips on the Film Thickness

Before the beginning of the experiment, the user needs to define a reference position in (X,Y,Z) in order to define the initial coordinates of the dispense and aspiration steps. The definition of (X,Y) coordinates is straightforward, knowing the coordinates of the centers of wells of a 96-well plate.

The following procedure was followed to control the Z-position of the tip at the vicinity of the plate bottom during solution dispense in the well and aspiration from the well. Prior to the beginning of the experiment, the tip was positioned in close vicinity to the bottom of the plate. The tip was first set in contact with the microplate until there was absolutely no movement possible for the microplate. Then, the tip was elevated in Z by one step (100 µm with the used robot). This position was set as reference Z position, Z0.

We thus investigated whether and how the Z-positioning of the tip influences the film thickness measurement. To this end, films were built at four different Z positions with stepwise increase of 0.3 mm from the reference position Z0 (ie 0.1 mm above the bottom of the plate) (FIGS. 26 to 29).

The dispersion in film thickness increased with Z for the NT conditions and the T_0% but the values remained almost independent of Z for the T_10% condition. Therefore, this latter condition appears to be more flexible for the user, who does not need to be highly precise in the optimization of Z0.

As regards the "Surface Wet" condition, since there is a permanent liquid film inside each well, there is no need to precisely adjust the initial Z-position Z0 of the pipette tip prior to the experiments.

Example 2

Automated (PSS/PAH) or (CHI/PGA) Film Buildup Using a Liquid Handling Machine

The automated deposit method was also applied to other types of polyelectrolyte films. We selected a polyelectrolyte system, namely (PSS/PAH) films, that is known to grow linearly and is considered as a "model system". As anticipated, their dry thickness was found to growth linearly with the number of deposited layer pairs (FIG. 33) up to around 250 nm for a film made of 40 pairs of layers.

We also checked for another polyelectrolyte system made of (CHI/PGA) that the polyelectrolyte film can be efficiently deposited at the bottom of the wells. The thickness of a (CHI/PGA) 12 film was 2.26±0.14 µm as measured from confocal microscopy imaging.

Example 3

Bioactive Proteins Loading in (PLL/HA) Films

The homogeneity of proteins that were post-loaded in the polyelectrolyte films prepared in examples 1 and 2 was assessed.

Film Crosslinking and Loading of Bioactive Proteins in (PLL/HA) Films

Bioactive proteins were loaded in (PLL/HA) films as previously described in Crouzier T at al., Small 2009, 5:598-608.

The films were first chemically crosslinked in a 0.15 M NaCl solution at pH 5.5 using 1-Ethyl-3-(3-Dimethylaminopropyl)Carbodiimide (EDC, final concentration of 10, 30 or 70 mg/mL) and N-Hydrosulfosuccinimide sodium salt (Sulfo-NHS, final concentration of 11 mg/mL) as catalyzer. The films were incubated at 4° C. overnight, then thoroughly washed the HEPES-NaCl buffer.

The (PLL/HA) polyelectrolyte films were manually loaded with bone morphogenetic proteins (BMP-2, BMP-7, BMP-4, BMP-9 or two BMP chimeras, namely chimera 1 and chimera 2) as bioactive proteins at acidic pH using a multi-channel pipette, following as previously described in Crouzier T at al., Small 2009, 5:598-608.

Cell Culture and Cell Response to the Bioactive Polyelectrolyte Films

We used BMP-2 responsive cells, C2C12 skeletal myoblasts (<25 passages, obtained from the American Type Culture Collection, ATCC), to assess the bioactivity of the polyelectrolyte films. Cells were cultured as previously described (Crouzier T at al., Small 2009, 5:598-608) in tissue culture Petri dishes, in a 1:1 Dulbecco's Modified Eagle Medium (DMEM):Ham's F12 medium (Gibco, Invitrogen, France) supplemented with 10% fetal bovine serum (FBS, PAA Laboratories, France) and 100 U/mL penicillin G and 100 µg/mL streptomycin (Gibco, Invitrogen, France) in a 37° C., 5% $CO_2$ incubator. Then, 15 000 cells/cm$^2$ in their medium were seeded in each well. After 4 h and 24 h of adhesion, phase contrast images were acquired and the samples were also fixed in 4% paraformaldehyde (Sigma Aldrich, St Quentin Fallavier, France). The nuclei were stained using DAPI (Life technologies and the actin cytoskeleton using Rhodamine-phalloidin (Sigma Aldrich).

D1 Murine Mesenchymal Stem Cell (D1) Culture

D1 cell culture was first done for 2 days in growth medium (89% aMEM (sigma M4526), 10% FBS with 1% antibiotics (penicillin streptomycin mix, 15140122 Invitrogen)) followed by 7 days in differentiation medium (growth medium supplemented with 50 µg/ml L-Ascorbic acid 2-phosphate and sesquimagnesium salt hydrate (Sigma A8960) and 10 mM β-Glycerol phosphate disodium salt pentahydrate (Sigma 50020). 9375 cells were seeded in each well. After the cell culture was stopped, ALP activity was assessed via enzymatic assay.

Human Periosteum Derived Stem Cells (hPDSQ) Culture

Human periosteum derived stem cells (passage between 10 and 14) were cultured in DMEM/high glucose in the presence of 10% FBS in the presence of 250 µM ascorbic acid 2 phosphate. They were seeded at a density a 5000 cells/cm2 (~1700 cells per well) in 200-µL of medium. The medium was changed every 2-3 days and the cell culture was done for 2 weeks.

Alkaline Phosphatase (ALP) Bioactivity

After a given number of days of culture, (3 days for C2C12, 3 for D1 cells and 14 for hPDSC) the growth medium was removed and the cells were fixed with 4% paraformaldehyde. They were stained for ALP activity fast blue RR salt in a 0.01% (w/v) naphthol AS-MX solution (Sigma Aldrich) according to the manufacturer's instructions.

ALP Enzymatic Activity.

The culture medium was removed and the cells were washed with PBS and lysed by sonication over 5 s in 500 mL of 0.1% Triton-X100 in PBS. The ALP activity of these lysates was then quantified using standard protocol and normalized to the corresponding total protein content, which was determined using a bicinchoninic acid protein assay kit (Interchim, France).

Analysis of the Homogeneity of Bioactive Proteins Loaded in the Polyelectrolyte Films In order to assess the homogeneity of BMP-2 loading in the (PLL/HA) films, BMP-2 labelled with carboxy fluorescein (BMP-2CF) was used (5% of the total BMP-2 concentration) and tile scans of the wells were performed in the Hepes-NaCl buffer after thorough rinsing of the films in order to get only matrix-bound BMP-2.

The bioactivity of the BMP proteins was assessed using BMP-responsive cells.

To begin, we chose to work with films crosslinked with an EDC final concentration of 30 mg/mL (i.e. noted EDC30 since these films are known to be poorly adhesive for cells, unless they are presenting BMP-2 in a matrix-bound manner. The more heterogeneous the film is, the more differences in the cell response to matrix-bound BMPs is expected.

Since matrix-bond BMP-2 on EDC30 films drastically increases cell adhesion and spreading, we first assessed cell adhesion at 24 h. (FIG. 30).

For these experiments, the two "extreme conditions" of NT_10% and T_10% were selected and the Surface Wet condition.

Cells appeared to be round and poorly adherent on the NT_10% conditions while they were more numerous and also more spread in the T_10% condition.

BMP-2 bioactivity can be quickly assessed by staining for the expression of an early bone marker, the alkaline phosphatase (FIG. 31). All conditions lead to a BMP-2 dose-dependent and significant ALP expression, as can been seen after cell staining and corresponding quantifications.

High Throughput Screening of Stem Cell Adhesion and Fate

We selected the T_10% condition to further prove the versatility of the matrix-bound proteins to screen for cellular processes on stem cells at high throughput.

We first tested whether matrix-bound BMP-7 was bioactive toward murine D1 stem cells (FIG. 32). To this end, the cells were cultured for up to 9 days on the bioactive polyelectrolyte films. We found that cells selectively adhere on the matrix-bound BMP-7 and could growth for up to at least 9 days. Of note, cells detached in the absence of matrix-bound BMP-7 and formed nodules in its presence. Their ALP expression directly depended on the amount of matrix-bound BMP-7 and grow exponentially to a plateau value (fit in the graph of FIG. 32).

We further tested whether matrix-bound BMPs are bioactive toward murine C2C12 skeletal myoblasts (FIGS. 34 and 35).

To this end, we first verified that these BMPs could be effectively loaded in the biomimetic films (Table 4).

TABLE 4

Proportion and quantity of BMP loaded in the (PLL/HA) films.

| | % incorporated | Quantity (ng/cm$^2$) | SD |
|---|---|---|---|
| BMP-9 | 86% | 2325 | 65 |
| BV-265 | 61% | 1850 | 56 |
| BMP-2 | 60% | 1650 | 115 |
| BMP-4 | 65% | 1810 | 15 |
| BMP-7 | 38% | 1100 | 84 |

The cells were cultured for 3 days on the bioactive polyelectrolyte films (5 different BMP proteins and 4 different BMP loading concentrations). We found that cells selectively adhere on the matrix-bound BMPs and grow on this time period. Their ALP expression was assessed at high throughput using two different methods: first, ALP staining was visualized using a scanner and images of the whole microplate were taken, showing the ALP expression in each individual well (FIG. 34). Second, ALP staining was quantified at high throughput using a Tecan Infinite 1000 microplate reader, by quantifying the absorbance at 570 nm using multiple-read per well mode (76 different positions were measured in each individual microwell and the mean value of these 76 positions was taken). This quantification enables to plot the ALP as a function of the initial concentration of the BMPs in solution (FIG. 35), which clearly shows a dose-dependent ALP response: the ALP intensity depends on the type of BMPs (in the order BMP-9>BV265>BMP-2>BMP-4>BMP-7) and on the dose of BMPs (increased ALP expression with the increased BMP concentration). The corresponding exponential fits toward a plateau value (continuous and dashes lines) are also given for BMP-2, BMP-9, BV265, BMP-4 while the fit was linear for BMP-7 (continuous line).

Example 4

Automated (PLL/PGA) Film Buildup Using a Liquid Handling Machine and High Throughput Screening of Cell Adhesion and Spreading The automated deposit method was also applied to another type of polyelectrolyte films, namely (PGA/PLL) films that we previously studied for cell adhesion (Picart et al, *Adv. Funct Mat* 2005).

For this study, we used films made only using the T_10% condition.

The (PGA/PLL) films were made of 5 layer pairs (eg (PGA/PLL) 5 films) and were either native (eg not crosslinked, CL 0) or crosslinked to different extents (EDC 5, EDC10, EDC30 named hereafter as CL5, CL10, CL30). So, in total, there were 4 different films conditions. They were finally rinsed with the Hepes-NaCl buffer using the liquid handling machine. On top of these films, a final layer was deposited. It is constituted of a mixture of PGA and PGA-RGD peptide (a RGD containing peptide grafted to the PGA) at fixed proportions. The PGA/PGA-RGD ratio used for the deposit of the final layer was varied in order to study 4 different conditions for the final layer: P0 (3/0); P1 (2/1); P2 (1/2); P3: 0/3). C2C12 myoblast C2C12 were seeded in the 96-well microplates at a density of 3500 cells/well (around 10500 cells/cm2).

We first verified that the biomimetic films were homogeneous inside each well as observed using the tile scan option of the microscope (FIG. 36, showing the whole well of about 6 mm in diameter).

Cell adhesion and spreading was next quantified after 1H of cell culture on top of the different biomimetic films in the serum-free medium. To do so, their nucleus (stained with Hoechst) and cytoskeleton (stained with rhodamine phalloidin) were stained. Images were automatically acquired at high throughput at 20× objective in the two channels using an automated Zeiss fluorescence microscope. The number of adherent cells increases with the concentration of the RGD-peptide for the uncrosslinked films (CL 0) and films crosslinked at low extent (CL 5) but was peptide-independent for the more CL films (CL 10 and CL30) (FIG. 37). Regarding the cell spreading area (FIG. 38), a clear peptide-dependent cell spreading area was visible, with an enhanced myoblast spreading when the quantity of peptide increased. We can thus conclude that the (PGA/PLL) biomimetic films containing a peptide-grated layer can be used to do cell adhesion and spreading at high throughput.

What is claimed is:

1. A method for coating the bottom surface of at least one well of a multiwell plate by a polyelectrolyte multilayer film, said method comprising n successive sequences, n being an integer from 1 to 2000, wherein each sequence comprises the steps of:
    a) robotic deposit of a volume $V_{PE}^1$ of a solution of a first polyelectrolyte $PE^1$ on the bottom surface of at least one well of a multiwell plate, wherein the first polyelectrolyte $PE^1$ is either a cationic polymer comprising amino groups, or an anionic polymer, then
    b) robotic aspiration of an aspirated volume $V_{aspPE}^1$ of said solution of $PE^1$, wherein the aspirated volume $V_{aspPE}^1$ is higher than or equal to $V_{PE}^1$, then
    c) robotic deposit of a volume $V_{PE}^2$ of a solution of a second polyelectrolyte $PE^2$ on said bottom surface, wherein the second polyelectrolyte $PE^1$ is a cationic polymer comprising amino groups when $PE^1$ is an anionic polymer, or $PE^2$ is an anionic polymer when $PE^1$ is a cationic polymer comprising amino groups, then
    d) robotic aspiration of an aspirated volume $V_{aspPE}^2$ of said solution of $PE^2$, wherein the aspirated volume $V_{aspPE}^2$ is higher than or equal to $V_{PE}^2$.

2. The method according to claim 1, wherein each sequence comprises:
    between steps a) and b), a step a') of incubation wherein the solution of first polyelectrolyte $PE^1$ is left in contact with the bottom surface for a duration from 1 to 30 minutes, and
    between steps c) and d), a step c') of incubation wherein the solution of second polyelectrolyte $PE^2$ is left in contact with the bottom surface for a duration from 1 to 30 minutes.

3. The method according to claim 1, wherein each sequence comprises:
    between steps b) and c), a rinsing step comprising the following substeps:
    b2) robotic deposit of a volume $V_{rinsePE}^1$ of a rinsing solution on said bottom surface, then
    b3) robotic aspiration of an aspirated volume $V_{asprinsePE}^1$ of said rinsing solution, wherein the aspirated volume $V_{asprinsePE}^1$ is higher than or equal to $V_{rinsePE}^1$,
    wherein the rinsing step can be repeated, and
    after step d), a rinsing step comprising the following substeps:
    d2) robotic deposit of a volume $V_{rinsePE}^2$ of a rinsing solution on said bottom surface, then
    d3) robotic aspiration of an aspirated volume $V_{asprinsePE}^2$ of said rinsing solution, wherein the aspirated volume $V_{asprinsePE}^2$ is higher than or equal to $V_{rinsePE}^2$,
    wherein the rinsing step can be repeated.

4. The method according to claim 3, wherein each sequence comprises:
    between steps b2) and b3), a step b2') of incubation wherein the rinsing solution is left in contact with the bottom surface for a duration from 0.2 to 10 minutes, and
    between steps d2) and d3), a step d2') of incubation wherein the rinsing solution is left in contact with the bottom surface for a duration from 0.2 to 10 minutes.

5. The method according to claim 1, wherein prior to step a) of the first sequence, said at least one well is filled with a volume $V_{wet}$ of the solution of the first polyelectrolyte $PE^1$, wherein the volume $V_{wet}$, expressed in mL, is from:

$$V_{wet}{}^{min}=0.5\times\pi(d/2)^2$$

to $$V_{wet}{}^{max}=(2/3)\times\pi(d/2)^2\times H,$$

wherein:
d is the diameter of the well, expressed in mm,
H is the height of the well, expressed in mm.

6. The method according to claim 5, wherein, at each sequence, $V_{aspPE}^1 = V_{PE}^1$ and $V_{aspPE}^2 = V_{PE}^2$.

7. The method according to claim 5, comprising, prior to step a) of the first sequence, a step a0) of robotic deposit of a volume $V_{wet}$ of the solution of the first polyelectrolyte $PE^1$ on the bottom surface of each well on which the deposit will be carried out at step a) of the first sequence.

8. The method according to claim 5, comprising, prior to step a) of the first sequence, the steps of:
a1) robotic deposit of a volume $V_{a1)}$ of the solution of the first polyelectrolyte $PE^1$ on the bottom surface of each well on which the deposit will be carried out at step a) of the first sequence, wherein $V_{a1)}$ is higher than $V_{wet}$, then
a2) robotic aspiration of an aspirated volume $V_{a2)}$ of said solution of the first polyelectrolyte $PE^1$, wherein the aspirated volume $V_{a2)}$ is as such that:

$$V_{a2)} = V_{a1)} - V_{wet}.$$

9. The method according to claim 1, wherein, for each sequence, at steps a), b), c), d), and, if these steps are present, at steps b2), b3), d2) and d3), the bottom surface is tilted with an inclination angle α from 5 to 40° relative to the horizontal plane.

10. The method according to claim 2, wherein, for each sequence, at steps a), b), c), d), and, if these steps are present, at steps b2), b3), d2) and d3), the bottom surface is tilted with an inclination angle α from 5 to 40° relative to the horizontal plane, and wherein, for each sequence, at steps a') and c'), the bottom surface is within the horizontal plane.

11. The method according to claim 9, wherein, at each sequence, the aspirated volume $V_{aspPE}^1$ is from $1.05\,V_{PE}^1$ to $1.20\times V_{PE}^1$ and the aspirated volume $V_{aspPE}^2$ is from $1.05\,V_{PE}^2$ to $1.20\times V_{PE}^2$.

12. The method according to claim 1, wherein the anionic polymer comprises carboxylic groups, said method comprising, after the n sequences, the following steps:
e) reacting said amino and carboxylic groups in the presence of a coupling agent, so as to form amide bonds and to cross-link the polyelectrolyte multilayer film, then
f) treating said cross-linked polyelectrolyte multilayer film with a protein containing solution, so as to incorporate said protein on and inside said cross-linked polyelectrolyte multilayer film.

13. The method according to claim 12, comprising, between steps e) and f) or after step f), a step g) of drying the polyelectrolyte multilayer film.

14. The method according to claim 1, comprising, after the n sequences, a step e') of robotic deposit of a volume $V_{PE}^3$ of a solution of a third polyelectrolyte $PE^3$ on said bottom surface, wherein:
polyelectrolyte $PE^3$ is linked to at least a peptide, and
the third polyelectrolyte $PE^3$ is a cationic polymer comprising amino groups when $PE^2$ is an anionic polymer, or $PE^3$ is an anionic polymer when $PE^1$ is a cationic polymer comprising amino groups.

15. The method according to claim 4, wherein, for each sequence, at steps a), b), c), d), and, if these steps are present, at steps b2), b3), d2) and d3), the bottom surface is tilted with an inclination angle α from 5 to 40° relative to the horizontal plane, and wherein, for each sequence, at steps b2') and d2'), the bottom surface is within the horizontal plane.

* * * * *